US 11,224,858 B1

United States Patent
Josephs et al.

(10) Patent No.: US 11,224,858 B1
(45) Date of Patent: Jan. 18, 2022

(54) REDUCED LEACHING OF A LIGAND

(71) Applicant: Immunicom, Inc., San Diego, CA (US)

(72) Inventors: Steven Josephs, San Diego, CA (US); Amir Jafri, San Diego, CA (US); Mark Raptis, San Diego, CA (US)

(73) Assignee: IMMUNICOM, INC., San Diego, CA (US)

( * ) Notice: Subject to any disclaimer, the term of this patent is extended or adjusted under 35 U.S.C. 154(b) by 0 days.

(21) Appl. No.: 17/219,764

(22) Filed: Mar. 31, 2021

Related U.S. Application Data

(63) Continuation-in-part of application No. 17/061,246, filed on Oct. 1, 2020.

(51) Int. Cl.
| | | |
|---|---|---|
| B01J 20/30 | (2006.01) | |
| B01J 20/32 | (2006.01) | |
| A61M 1/34 | (2006.01) | |
| B01J 20/24 | (2006.01) | |

(52) U.S. Cl.
CPC ........ *B01J 20/3274* (2013.01); *A61M 1/3496* (2013.01); *B01J 20/24* (2013.01); *B01J 20/3085* (2013.01); *B01J 20/328* (2013.01); *B01J 20/3219* (2013.01); *B01J 20/3285* (2013.01)

(58) Field of Classification Search
CPC ...... B01J 20/24; B01J 20/3085; B01J 20/328; B01J 20/3274; B01J 20/3285; B01J 20/3219; A61M 1/3496
See application file for complete search history.

(56) References Cited

U.S. PATENT DOCUMENTS

| | | |
|---|---|---|
| 3,947,352 A | 3/1976 | Cuatrecasas et al. |
| 5,486,463 A | 1/1996 | Lesslauer et al. |
| 6,379,708 B1 | 4/2002 | Howell et al. |
| 6,569,112 B2 | 5/2003 | Strahilevitz |
| 6,645,388 B2 | 11/2003 | Sheikh-Ali |
| 7,775,376 B2 | 8/2010 | Bonaguidi et al. |
| 8,137,988 B2 | 3/2012 | Rife et al. |
| 8,501,918 B2 | 8/2013 | Howell |

(Continued)

FOREIGN PATENT DOCUMENTS

| | | |
|---|---|---|
| EP | 3669888 A1 | 6/2020 |
| WO | 2007084452 A2 | 7/2007 |

(Continued)

OTHER PUBLICATIONS

G-Biosciences Application Note 8, Generation of Protein Affinity Columns That Reduce Protein Leaching, downloaded May 21, 2020 from www.GBiosciences.com, pp. 1-2.

(Continued)

*Primary Examiner* — John Kim
(74) *Attorney, Agent, or Firm* — Pillsbury Winthrop Shaw Pittman LLP

(57) ABSTRACT

A column for removal of a component from a fluid is disclosed. The column has a compartment with a cross sectional area. The compartment contains beads having a diameter. A ligand selected to bind to the component is coupled to the beads. The cross-sectional area and bead diameter are selected to maintain a flow velocity of the fluid within the compartment below a first threshold, thereby reducing leaching of the ligand into the fluid. Also described herein is an adsorbent comprising a ligand that is attached to a substrate by an amine bond, wherein the ligand is resistant to dissociation from the substrate.

10 Claims, 10 Drawing Sheets

Specification includes a Sequence Listing.

(56) References Cited

U.S. PATENT DOCUMENTS

| | | |
|---|---|---|
| 8,663,148 B2 | 3/2014 | Larm et al. |
| 8,758,286 B2 | 6/2014 | Ward et al. |
| 2004/0265392 A1 | 12/2004 | Tovar et al. |
| 2005/0148748 A1 | 7/2005 | Tanaka et al. |
| 2009/0099344 A1 | 4/2009 | Fahrner et al. |
| 2010/0249689 A1 | 9/2010 | Larm et al. |
| 2013/0264288 A1 | 10/2013 | Hlavinka et al. |
| 2014/0074007 A1 | 3/2014 | McNeil |

FOREIGN PATENT DOCUMENTS

| | | |
|---|---|---|
| WO | 2007/103572 A2 | 9/2007 |
| WO | 2008/039361 A2 | 4/2008 |
| WO | 2010/033249 A2 | 3/2010 |
| WO | 2011059786 A1 | 5/2011 |
| WO | 2012/163544 A1 | 12/2012 |
| WO | 2013/043070 A2 | 3/2013 |
| WO | 2016/193986 A2 | 12/2016 |
| WO | 2017/189899 A1 | 11/2017 |
| WO | 2019243439 A1 | 12/2019 |
| WO | 2021/101519 A1 | 5/2021 |

OTHER PUBLICATIONS

Marochkin, et al., Amide Bond Dissociation Enthalpies: Effect of Substitution on N—C strength, Computational and Theoretical Chemistry, 2012, pp. 182-191, 991.

Lalevee, et al., N—H and α(C—H) Bond Dissociation Enthalpies of Aliphatic Amines, Journal of American Chemical Society, Jul. 16, 1992, pp. 9613-9621, 124.

Hermanson, G. T. et al., Immobilized Affinity Ligand Techniques, table 2.4, 1992, p. 913 of 4617 (Kindle), Academic Press.

Gray, "Affinity Chromatography", Anal. Chem., 1980, pp. 9R-15R, vol. 52.

Patent Cooperation Treaty, International Search Report and Written Opinion issued in PCT/US2020/053847, Oct. 11, 2021, pp. 1-31.

Josephs et al., "Unleashing endogenous TNF-alpha as a cancer immunotherapeutic", Journal of Translational Medicine, Dec. 1, 2018, pp. 1-8.

Margel et al., "Agarose-polymeric microsphere beads: Specific new adsorbents for hemoperfusion", Reactive Polymers, Ion Exchangers, Sorbents, Oct. 1, 1983, pp. 241-250, vol. 1(4).

Margel, "Polyacrolein Microspheres", Biomembranes: Transport Theory: Cells and Model Membranes, Jan. 1, 1985, pp. 164-174, vol. 112.

Hermanson, "Bioconjugate Techniques (3rd Edition)—Chapter 3", Nov. 1, 2013, pp. 229-258, Academic Press, ProQuest ebrary, Web, XP005258103.

Enlarged View of "A"

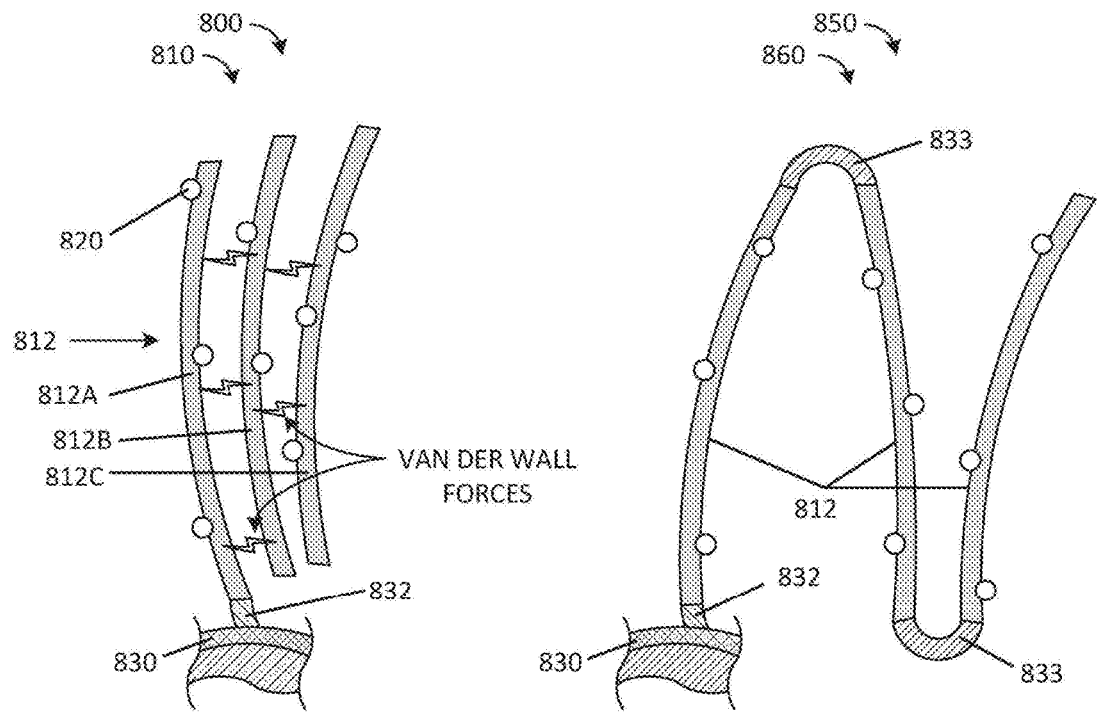
Figure 8A
Figure 8B
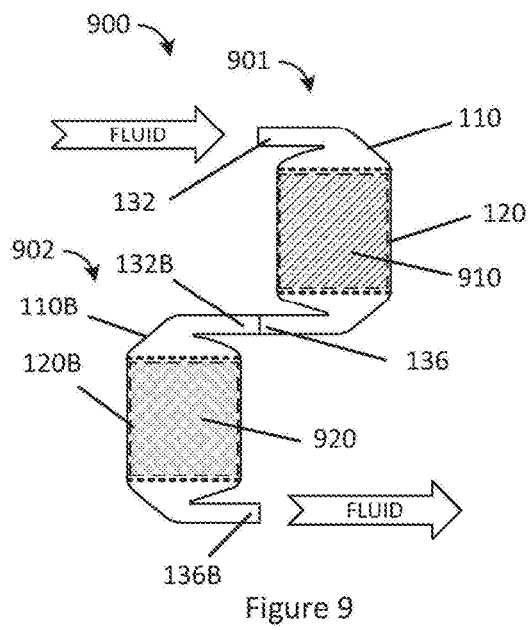
Figure 9

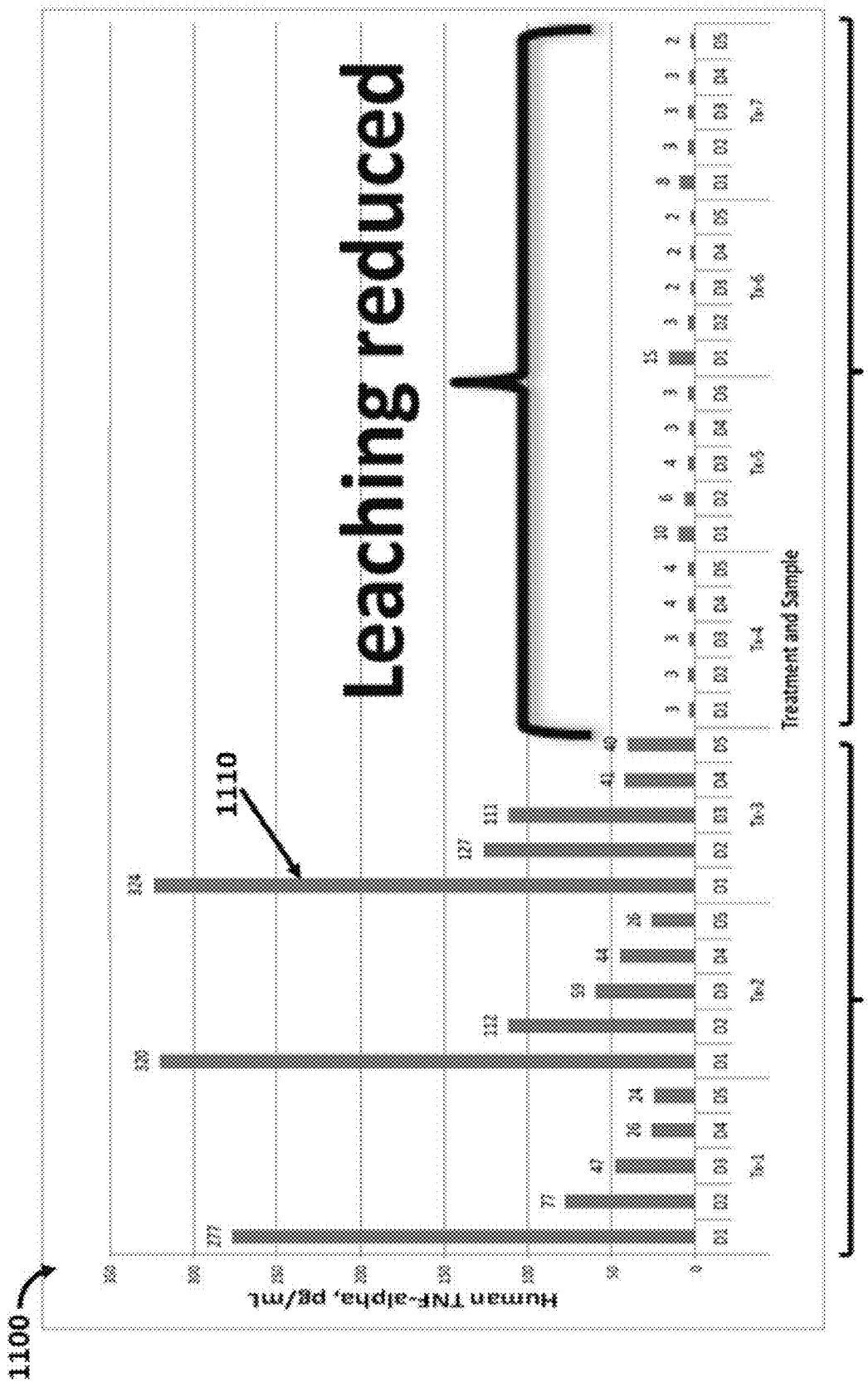

REDUCED LEACHING OF A LIGAND

RELATED APPLICATIONS

This patent application is a continuation-in part of U.S. patent application Ser. No. 17/061,246, filed Oct. 1, 2020. The entire content of the foregoing patent application is incorporated herein by reference, including all text, tables and drawings.

SEQUENCE LISTING

The present application is being filed with a Sequence Listing. The Sequence Listing is submitted electronically in ASCII format via EFS-Web in the form of a text file. Said ASCII copy, created on Mar. 31, 2021, is named "IMMU-NICOM-0560631-US.txt" and is 10.2 KB in size, the contents of which are incorporated herein by reference in their entirety.

INTRODUCTION

Apheresis is a medical technology in which the blood of a patient is passed through an apparatus that separates out one or more particular constituents and returns the remainder to the circulatory system. It is thus an extracorporeal therapy. This technology is commonly used to collect platelets at blood donation centers.

The body's control of inflammation and cellular apoptosis is a complex process that is managed by a multitude of regulatory proteins. Tumor necrosis factor alpha (TNF-alpha) is a potent cytokine that has been characterized as an anti-tumor agent. The natural control of TNF-alpha's effects is attributed to the presence of inhibitory molecules, for example soluble TNF-alpha receptors (sTNF-Rs) such as sTNF-R1 and sTNF-R2, in the plasma. The soluble receptors can bind to and neutralize TNF-alpha.

Attempts to remove sTNF-Rs from the blood have led to reports of leaching of potentially dangerous amounts of column materials into a patient's bloodstream, variability in the removal of sTNF-Rs, side effects, and complications that have raised doubt as to whether the current state of apheresis is a practical therapeutic approach.

SUMMARY

It is desirable to provide a "subtractive" immunotherapy designed to remove inhibitory molecules from a patient's circulation, thereby enabling the body's natural immune response while avoiding leaching of the column materials into the processed blood component. In certain embodiments, it is desirable to remove sTNF-Rs from a patient's circulation, thereby boosting the activity of TNF-alpha against neoplastic cells.

A column for removal of a component from a fluid is disclosed. The column includes a compartment having a cross-sectional area, a bead having a diameter and disposed within the compartment, and a ligand coupled to the bead and selected to bind to the component. The cross-sectional area and bead diameter are selected to maintain a flow velocity of the fluid within the compartment below a first threshold.

A method of removing a component from blood of a patient is disclosed. The method includes the steps of receiving blood from the patient, separating the blood into at least two blood components, and passing a portion of one of the components through a compartment having a cross sectional area and containing a plurality of beads having a diameter and to which are coupled a ligand selected to bind to the component. The cross-sectional area and bead diameter are selected to maintain a flow velocity of the blood component within the compartment below a first threshold. The method also includes the steps of mixing the at least two blood components together and returning the mixed blood components to the patient.

A ligand for removal of a component from a fluid is disclosed. The ligand includes at least two monomers each having a site that will couple to the component, a first linker between two of the monomers, and a second linker coupled to one of the monomers and coupled by a chemical bond to the substrate.

A substrate for use in removing a component from a fluid is disclosed. The substrate has a ligand coupled to the substrate. The ligand can comprise at least two monomers each comprising a site that will couple to the component, a first linker coupled between two of the monomers, and a second linker coupled to one of the monomers and coupled by a chemical bond to the substrate.

A column for use in removing a component from a fluid is disclosed. The column has a compartment and a substrate disposed within the compartment. The substrate has a ligand coupled to the substrate. The ligand can comprise at least two monomers each having a site that will couple to the component. The ligand also includes a first linker coupled between two of the monomers and a second linker coupled to one of the monomers and coupled by a chemical bond to the substrate.

A method of removing a target component from blood of a patient is disclosed. The method includes the steps of receiving blood from the patient, separating the blood into at least two blood components, and passing a portion of one of the blood components proximate to a ligand. The ligand has at least two monomers each having a site that will couple to the component. The ligand also has a first linker coupled between two of the monomers and a second linker coupled to one of the monomers and coupled by a chemical bond to the substrate. The method also includes the steps of mixing the at least two blood components together and returning the mixed blood components to the patient.

A method of preparing a bead for use in apheresis is disclosed. The method includes the steps of oxidizing a substrate, forming a Schiff base between a ligand comprising a portion of TNF-alpha and the oxidized substrate, and converting the Schiff base to a secondary amine bond.

The apparatus and methods disclosed herein have been shown in vivo and in vitro to efficiently remove sTNF-Rs from plasma, providing a positive clinical impact on certain cancer tumors while avoiding the negative effects of TNF-alpha leaching from the column into the plasma returned to the patient, as seen in currently available systems. The same apparatus and methods are applicable to other target components and treatment of other conditions.

In some aspects, presented herein is an adsorbent for removing a target component from blood of a subject, the adsorbent comprising a substrate comprising a surface; a linker comprising an amine bond; and a ligand comprising TNFα; where the linker is attached to the substrate and to the ligand.

In some aspects, presented herein is an adsorbent for removing a TNF receptor from blood of a subject, where the adsorbent comprises a substrate comprising a substrate surface; and a ligand comprising a single chain TNFα; where the substrate surface is attached to the single chain TNFα by an amine bond (e.g., a secondary amine bond). In some embodiments, the substrate surface comprises a polysaccharide.

DESCRIPTION OF THE DRAWINGS

FIGS. 8A-8B depict schematic examples of ligands comprising trimers, according to certain aspects of this disclosure.

FIG. 9 depicts a 2-stage column, according to certain aspects of this disclosure

DETAILED DESCRIPTION

Figure 1:
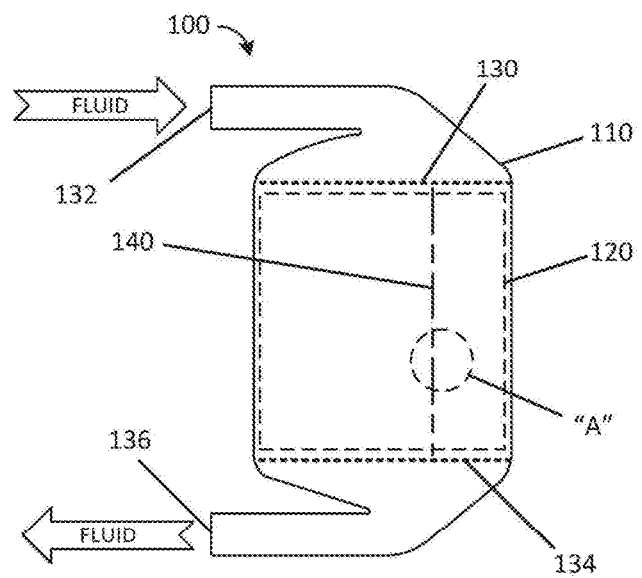
FIG. 1 depicts an exemplary apheresis column.

The following description discloses embodiments of an apheresis column and portions thereof. In certain embodiments, a column is used in conjunction with an apheresis machine, for example one of the machines currently used at blood donor centers. A typical machine extracts whole blood from a patient and separates the blood into blood components, for example red blood cells, platelets and white cells, and plasma. One of the blood components, for example the plasma, may be passed through the column to remove a target material. The processed blood component and the remaining blood components then are integrated and re-introduced into the bloodstream of the patient.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be apparent to those skilled in the art that the subject technology may be practiced without these specific details. In some instances, well-known structures and components are shown in block diagram form to avoid obscuring the concepts of the subject technology. Like, or substantially similar, components are labeled with identical element numbers for ease of understanding.

As used within this disclosure, the term "patient" means any vertebrate organism having a circulatory system. A patient may be a human being. A patient may also be an animal such as a dog or cat or any other mammal.

As used within this disclosure, the term "fluid" means a composition that may comprise one or more miscible and/or immiscible liquid components, one or more dissolved gaseous components, and one or more solid or semi-solid components. A fluid may be a biological fluids such as blood, a blood component, or a portion thereof, such as plasma or serum, that may contain one or more of cells, antibodies, cytokines, peptides, proteins, and molecules such as sTNF-Rs.

As used within this disclosure, the phrase "blood component" means one of the fluids from which blood may be separated, for example by centrifugation. For example, blood can be separated into a first blood component that is primarily red cells, a second blood component that is primarily platelets and white cells, and a third component that is primarily plasma, although other types of separation are possible and included within this definition.

As used within this disclosure, the term "column" means a device through which passes a fluid from a patient, wherein the column contains material that interacts with the fluid. A column may be of various configurations in size and shape and comprise one or more adsorbents, substrates or ligands.

As used within this disclosure, the term "substrate" means an object that provides structure while not necessarily interacting with material proximate to the substrate. A substrate or surface of a substrate may comprise one or more organic materials, such as a polysaccharide, and also may comprise one or more inorganic materials, such as metal, plastic, ceramic, or water. A substrate may comprise a portion that has been converted to a different form, for example an oxide, by exposure to a substance, treatment, and/or environment. A substrate may comprise one or more layers, for example a coating or plating. A substrate may also be referred to as a "support."

In certain embodiments, a substrate comprises a particle (e.g., a bead). As used within this disclosure, the term "particle" is used to describe an exemplary structural embodiment of a substrate without excluding other geometric shapes or structures. A particle (e.g., bead) may be a solid form, such as a solid sphere, or have structure, such as a hollow element or an open-cell foam. A particle may comprise a simple geometric form, for example a sphere or rod, or a more complex form such as a "multi-arm star," e.g. a child's toy jack. In certain embodiments, a particle may comprise other materials, such as a ligand or a catalyst, intended to interact with material proximate to the particle. In certain embodiments, a particle comprises a bead.

In certain embodiments, a particle comprises a sphere. In certain embodiments, a particle comprising a sphere has a mean, average or absolute diameter in a range of about 1-600 µm. In certain embodiments, a particle comprising a sphere has a a mean, average or absolute diameter in a range of about 45-165 µm or in a range of about 60-200 µm. A particle can be porous or non-porous. In some embodiments, a particle is porous and comprises pores having a mean, average or absolute diameter in a range of about 10 nm to 100 nm. In some embodiments, a particle is a cellulose, e.g., agarose particle. In some embodiments, a particle is a SEPHAROSE™ particle.

As set forth herein, a substrate or particle (e.g., bead) often comprises a surface. In some embodiments, a surface comprises one or more carbons. In certain embodiments a surface, prior to attachment to a ligand, comprises one or more polysaccharides. In certain embodiments a surface, prior to attachment to a ligand, comprises one or more reactive carbons. In certain embodiments a surface, prior to attachment to a ligand, comprises one or more oxidized polysaccharides. In certain embodiments a surface, prior to attachment to a ligand, comprises one or more aldehyde moieties.

In certain embodiments a substrate or substrate surface comprises a polysaccharide. In certain embodiments a substrate or substrate surface comprises a cross-linked polysaccharide. In certain embodiments a substrate or substrate surface comprises a neutral or charged polysaccharide. In some embodiments, a substrate or substrate surface comprises cellulose (e.g., agarose), xylan, dextran, pullulan, starch, the like or a combination thereof. In some embodiments the substrate or substrate surface is modified to contain chemically active linking groups that can interact with ligand molecules to form stable chemical bonds. An example of this is a surface activation by exposing said substrate surface to sodium meta periodate which results in the formation of formyl groups that can participate in a reductive amination process with amine containing ligands [See Table 2].

As used within this disclosure, the term "surface" includes the conventional outer physical boundary of a 3D form as well as any portion of a substrate (e.g., an insoluble matrix) that is exposed to or may contact fluid passing through and proximate to the substrate and to which a ligand may be attached.

As used within this disclosure, the term "diameter" is used to identify a major dimension of a structural embodiment that affects the flow of a liquid through a volume containing one or more instances of the structural element. In an embodiment having a simple structure, for example a solid spherical bead, the diameter may be the common definition of the length of a line from one surface to another that passes through the center. In an embodiment having internal structure, for example an open-cell foam where a single instance may fill a volume, the diameter may be the average width of passages through the foam. In an embodiment having a complex structure, for example multi-arm stars, the diameter may be the average center-to-center separation of instances of the structure when piled on top of one another.

As used within this disclosure, the phrase "target component" means a chemical, compound, and/or organic structure with which a ligand is intended to interact. Example interactions may include capture of a target component. In particular, a target component may be an organic structure that is desired to be removed from the fluid passing through the column. In some embodiments, a target component is a soluble receptor, for example a soluble TNF receptor.

The term "ligand" means a material that possesses an affinity to bind to a target component. An example is binding of a site on the ligand to all or a portion of a target component. In certain embodiments, a ligand is non-detachably bound to a substrate. Binding of a target component to a non-detachably bound ligand is intended to retain the target component on the substrate.

As used within this disclosure, the terms "detachable" and "non-detachable" refer to the intended function of having a molecule attached to a substrate during a process, which is related to the ease with which the molecule may be released from that substrate. An attachment may be broken by chemical, physical or mechanical means. A molecule with an easily broken attachment that is intended to release the attached molecule during the process is considered detachable. A molecule with a relatively strong attachment that is intended to retain the attached molecule during the process is considered non-detachable. Modifying the attachment, for example through a non-reversible chemical change, may convert a detachable molecule into a non-detachable molecule without affecting other characteristics of the molecule.

As used within this disclosure, the term "ligand" means an organic structure, for example a polypeptide or peptide, comprising one or more elements having binding affinity for a target component. The elements may comprise one or more of an organic structure, such as recombinant single-chain TNF-alpha (scTNF-alpha). Elements may be connected in series or as multi arm branches. Elements may be coupled to each other via various bonding mechanisms that include covalent bonds, ionic bonds, hydrophobic bonds and Van der Waals forces, and may comprise chemicals, organic or inorganic compounds, or other elements in intermediate or terminal positions. A ligand can be a biological ligand such as a naturally occurring ligand, a synthetic ligand (e.g., artificially made, e.g., chemically synthesized) and/or a recombinantly produced ligand.

In some embodiments, a ligand binds specifically to a biological receptor. In some embodiments a ligand is a soluble ligand (e.g., not membrane bound). In some embodiments a ligand comprises an extracellular portion of a ligand. In some embodiments a ligand comprises a receptor-binding portion of a ligand.

In certain embodiments, a ligand comprises TNFα (e.g., UniProtKB accession no. P01375), a receptor-binding portion thereof, a receptor-binding variant thereof, a receptor-binding fusion protein thereof, the like, and combinations thereof. Naturally occurring TNFα comprises three substantially identical monomers assembled into a homotrimer, which may be membrane bound or soluble. Soluble TNFα is naturally produced by cleavage of the transmembrane portion of the TNFα monomers from a cell surface. Both membrane-bound and soluble TNFα can bind to its cognate receptors (i.e., TNFR1 (TNF receptor type 1; TNFRSF1A; CD120a; p55/60) and TNFR2 (TNF receptor type 2; TNFRSF1B; CD120b; p75/80). Accordingly, the transmembrane portion of TNFα is not required for receptor binding. Both TNFα dimers and TNFα trimers can bind specifically to TNFR1 or TNFR2, regardless of whether the receptors are present in soluble or membrane bound form. TNFα dimers can be made by recombinantly expressing TNF monomers as a fusion protein with, e.g., an Fc portion of an antibody, where the Fc portion forms a stable dimer that in turn stabilizes the dimeric configuration of the TNF molecule.

In some embodiments, a TNFα is recombinantly produced as a single-chain dimer or single chain trimer, that can efficiently bind to TNFR1 or TNFR2. Non-limiting examples of single chain (sc) TNFα includes those described in U.S. Pat. No. 8,927,205, U.S. Patent Application Publication No. US 2011/0162095, and US 2014/0056843, the like, receptor binding derivatives thereof, and receptor binding portions thereof, all of which patents and patent application publications are incorporated by reference herein.

In some embodiments, a ligand comprises a human TNFα sequence, a dimer thereof, a trimer thereof, or a receptor-binding portion or derivative thereof, of one or more of SEQ ID NOs:1, 2 and/or 3 as shown below:

```
(SSSRTPSDKPVAHVVANPQAEGQLQWLNRRANALLANGVELRDNQLVVP

SEGLYLIYSQVLFKGQGCPSTHVLLTHTISRIAVSYQTKVNLLSAIKSPC

QRETPEGAEAKPWYEPIYLGGVFQLEKGDRLSAEINRPDYLDFAESGQVY

FGIIAL, SEQ ID NO: 1) - [processed TNF monomer, from Genbank Accession No. AQY77150.1];

Exemplary Trimeric form of TNFα:
(MCGSHHHHHHGSASSSSRTPSDKPVAHVVANPQAEGQLQWLNRRANALL

ANGVELRDNQLVVPSEGLYLIYSQVLFKGQGCPSTHVLLTHTISRIAVSY

QTKVNLLSAIKSPCQRETPEGAEAKPWYEPIYLGGVFQLEKGDRLSAEIN

RPDYLDFAESGQVYFGIIALGGGSGGGSGGGSGGGSSRTPSDKPVAHVV

ANPQAEGQLQWLNRRANALLANGVELRDNQLVVPSEGLYLIYSQVLFKGQ

GCPSTHVLLTHTISRIAVSYQTKVNLLSAIKSPCQRETPEGAEAKPWYEP

IYLGGVFQLEKGDRLSAEINRPDYLDFAESGQVYFGIIALGGGSGGGSGG

GSGGGSSSRTPSDKPVAHVVANPQAEGQLQWLNRRANALLANGVELRDNQ

LVVPSEGLYLIYSQVLFKGQGCPSTHVLLTHTISRIAVSYQTKVNLLSAI

KSPCQRETPEGAEAKPWYEPIYLGGVFQLEKGDRLSAEINRPDYLDFAES

GQVYFGIIAL, SEQ ID NO: 2); and

Another Exemplary Trimeric form of TNFα:
(GSASSSSRTPSDKPVAHVVANPQAEGQLQWLNRRANALLANGVELRDNQ

LVVPSEGLYLIYSQVLFKGQGCPSTHVLLTHTISRIAVSYQTKVNLLSAI

KSPCQRETPEGAEAKPWYEPIYLGGVFQLEKGDRLSAEINRPDYLDFAES

GQVYFGIIALGGGSGGGSGGGSGGGSSRTPSDKPVAHVVANPQAEGQLQ

WLNRRANALLANGVELRDNQLVVPSEGLYLIYSQVLFKGQGCPSTHVLLT

HTISRIAVSYQTKVNLLSAIKSPCQRETPEGAEAKPWYEPIYLGGVFQLE

KGDRLSAEINRPDYLDFAESGQVYFGIIALGGGSGGGSGGGSGGGSSSRT

PSDKPVAHVVANPQAEGQLQWLNRRANALLANGVELRDNQLVVPSEGLYL

IYSQVLFKGQGCPSTHVLLTHTISRIAVSYQTKVNLLSAIKSPCQRETPE

GAEAKPWYEPIYLGGVFQLEKGDRLSAEINRPDYLDFAESGQVYFGIIA

L, SEQ ID NO: 3).
```

A single chain TNFα may comprise the structure NH2-$T_1$-$L_1$-$T_2$-$L_2$-$T_3$-COOH, where $T_1$, $T_2$ and $T_3$ comprise a polypeptide sequence of a TNF monomer, a derivative thereof, or a portion thereof capable of binding to a TNF receptor when assembled into a dimer or trimer configuration; $L_1$ and $L_2$ comprise a monomer linking region; NH2 represent the N-terminus and COOH represent the C-terminus of the ligand.

In some embodiments, a derivative of a TNF monomer comprises one or more conservative amino acid substitutions, such that the derivative of the TNF monomer retains the ability to bind specifically and with relatively high affinity to a TNF receptor when compared to a native TNF monomer. Conservative amino acid substitutions may comprise amino acid analogues.

In some embodiments, a ligand comprises a linker or linking element. As used within this disclosure, the phrase "linker" or "linking element" means a compound or structure that couples between two different structures (e.g., a ligand and a substrate; a ligand and substrate surface, etc.).

In some embodiments, a linker comprises a suitable peptide linker. In some embodiments, a linker comprises a peptide linker comprising Glycine (G) and/or Ser (S) amino acids. In certain embodiments, a peptide linker comprises one or more units (e.g., 1 to 20 units) of GGGS or GGGGS, and combinations thereof. In certain embodiments, a peptide linker comprises (GGGS)n or (GGGGS)n, where n is 1, 2, 3, 4, 5 or 6. In some embodiments, one or both of the monomer linking regions is absent, or comprises a single covalent bond.

In some embodiments, a linker comprises one or more carbons covalently bonded to each other.

In certain embodiments, a TNFα ligand, or monomer thereof, comprises a receptor binding portion of a TNFα ligand, or monomer thereof. The receptor-binding ability of a derivative or monomer of a TNFα ligand can be determined using a suitable method, non-limiting examples of which include an ELISA using a plate-coated recombinant TNF receptor (e.g., an Fc receptor) and a tagged (e.g., histidine tagged, Flag-tagged) recombinant TNFα ligand, or a flow cytometry-based approach using cells that express a TNF receptor, which method includes contacting the cells with the tagged recombinant TNFα. Subsequent detection and/or quantitation of binding can be carried out using a labeled antibody to the tagged ligand. Such methods are considered routine in the art. Using such traditional methods, the receptor-binding ability of recombinant TNFα ligand comprising conservative amino acid substitutions, additions or deletions, can be tested without requiring undue experimentation.

Accordingly, in some embodiments, a TNFα ligand, or a receptor binding derivative or variant thereof, is a ligand that binds to its cognate receptor with an affinity (Kd) of at least about $1\times10^{-6}$, $1\times10^{-7}$, $1\times10^{-8}$, or $1\times10^{-9}$. In certain embodiments, a ligand comprises TNFα, a receptor-binding dimer thereof, a receptor-binding trimer thereof, or a receptor binding derivative or portion thereof, that binds specifically to its cognate receptor (e.g., TNFR1 or TNFR2) with an affinity (Kd) of at least about $1\times10^{-6}$, $1\times10^{-7}$, $1\times10^{-8}$, or $1\times10^{-9}$. In certain embodiments, a ligand comprises a human TNFα, a receptor-binding dimer thereof, a receptor-binding trimer thereof, or a receptor binding derivative or portion thereof, that binds specifically to its cognate receptor (e.g., human TNFRSF1A or human TNFRSF1B) with an affinity (Kd) of at least about $1\times10^{-6}$, $1\times10^{-7}$, $1\times10^{-8}$, or $1\times10^{-9}$ M.

The term "specifically binds" or "binds specifically" refers to a ligand that binds to a target component (e.g., receptor) in preference to binding other molecules or other peptides as determined by, for example, a suitable in vitro assay (e.g., an Elisa, Immunoblot, Flow cytometry, and the like). A specific binding discriminates over non-specific binding by about 2-fold or more, about 10-fold or more, about 100-fold or more, 1000-fold or more, 10,000-fold or more, 100,000-fold or more, or 1,000,000-fold or more.

As used within this disclosure, the phrase "binding" or "binding element" means a compound or chemical structure (e.g., ligand or ligand) that will attach to a target component. In the example of a TNF-R target component, the binding element may be a portion of TNF comprising a site that has affinity for and therefore binds to TNF-Rs.

As used within this disclosure, the term "leaching" means the loss or separation (e.g., dissociation) of a ligand, or portion thereof, from an adsorbent or substrate.

As used within this disclosure, the term "toxic" means that the fluid passing out a column's outlet contains an amount of a substance that is considered to present an unacceptable risk. In the case of blood received from a patient and processed then returned to the patient, there will be a level of a material in the processed blood that is sufficiently greater than the level of the material in the blood received from the patient to be considered a risk to the patient if returned to the patient.

FIG. 1 depicts an exemplary apheresis column 100 according to certain aspects of the present disclosure. The column 100 comprises a body 110 that comprises a compartment 120 having an inlet 130 and an outlet 134. In the example of FIG. 1, the compartment 120 is generally a right cylinder wherein the inlet 130 and outlet 134 are both planar circular disks. In certain embodiments, the cross-sectional shape of the compartment 120 may be oval, rectangular, or other regular or irregular or nonplanar geometric shape. In certain embodiments, the size and shape of one or both of the inlet 130 and outlet 134 may be different from the size and shape of the nominal cross-section of the compartment 120.

The compartment 120 has an idealized flow path 140 from the inlet 130 to the outlet 134 that, in the example of FIG. 1, is a straight line. In certain embodiments, the flow path 140 may have curved portions, corners, or other geometric features. The compartment 120 has a cross-sectional area that is perpendicular to the flow path 140 at a point along the flow path 140. In certain embodiments, the compartment 120 may have a different cross-sectional area at different points along the flow path 140.

In certain embodiments, fluid enters an entrance port 132 and is conveyed to the inlet 130. Similarly, in certain embodiments, fluid coming out of the outlet 134 is conveyed to an exit port 136. In use, the column may be oriented in any direction, including upside down, such that the direction of gravity in FIG. 1 may be in any direction.

In certain embodiments, one or both of the inlet 130 and outlet 134 comprise a porous wafer, commonly referred to as a "frit," that is fabricated by melting polyethylene beads together. The diameter of the beads and the degree of compression are chosen to produce an average pore size. In certain embodiments, the average pore size is 20 microns. In certain embodiments, the frit is formed by sintering beads comprising a metal or a ceramic, with the same effect.

It is generally desirable to select an average pore size for the frit that allows the largest elements present in the incoming fluid to pass through the inlet 130 and outlet 134, thereby avoiding clogging of the column 100. It is further desirable to select the average pore size to retain the substrates, such as the beads 150 of FIG. 2, within the compartment 120.

Figure 2:
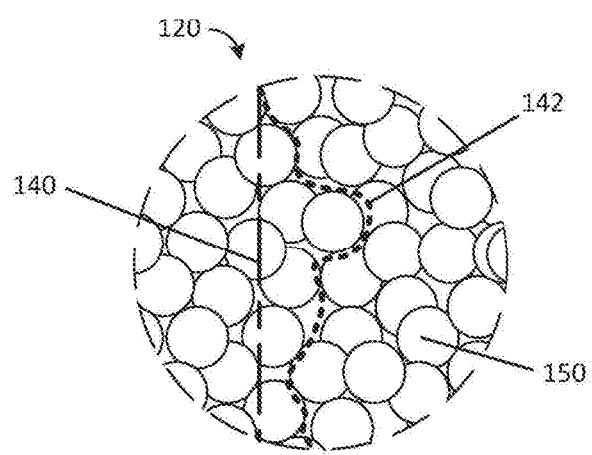
FIG. 2 depicts an enlarged view of an exemplary portion of the apheresis column of FIG. 1.

FIG. 2 depicts an enlarged view of an exemplary portion of the apheresis column 100 of FIG. 1, identified in FIG. 1 as "A," according to certain aspects of the present disclosure. In certain embodiments, the compartment 120 is at least partially filled with a substrate, for example a plurality of beads 150 as shown in FIG. 2. In certain embodiments, the beads 150 are spherical with a diameter that may be in a range of 10-10000 microns, 20-1000 microns, 30-500 microns, 40-250 microns, 45-165 microns, 75-125 microns, or other ranges of diameters. In certain embodiments, the beads 150 may have a common nominal diameter of 25, 50, 75, 100, 125, or 150 microns or other nominal diameter. In certain embodiments, the beads 150 may comprise a plurality of nominal diameters.

As fluid flows from the inlet 130 to the outlet 134, the actual flow path of the fluid will be a convoluted path, for example path 142 through the bed of beads 150. The length of path 142 will generally be longer than the length of the idealized flow path 140. The length of path 142 may be calculated or estimated.

In certain embodiments, the compartment 120 may contain a substrate comprising an open-cell foam. A single instance of the substrate may fill the compartment 120 or an entire cross-sectional area and a portion of the length of the compartment 120. In this case, the "diameter" of the substrate may be the average width of passages through the foam, as this passage width will determine the flow velocity of liquid passing through the substrate in a manner analogous to how the diameter of spherical beads determines the flow velocity of liquid passing through a compartment 120 filled with beads 150. Similarly, the actual flow path through an open-cell foam will be convoluted and have generally the same relationship to an idealized path 140 as described for the example of beads 150.

A flow velocity of the column 100 may be calculated using either of the true path 142 or the ideal flow path 140. One effect of this different in lengths is that the average velocity along path 142 will be higher than the average fluid velocity calculated using the idealized path 140. Second, the instantaneous velocity along path 142 may vary. Path 142 passes through channels having a variable open area based on the local packing arrangement of the beads 150. It is difficult, if not impossible, to accurately predict the actual fluid velocities along every point of the actual multitude of flow paths 142 through the compartment 120 of column 100. Experiments to determine a velocity-dependent characteristic, for example leaching of a ligand, must be conducted as discussed further with respect to FIG. 6.

Figures 3, 4:
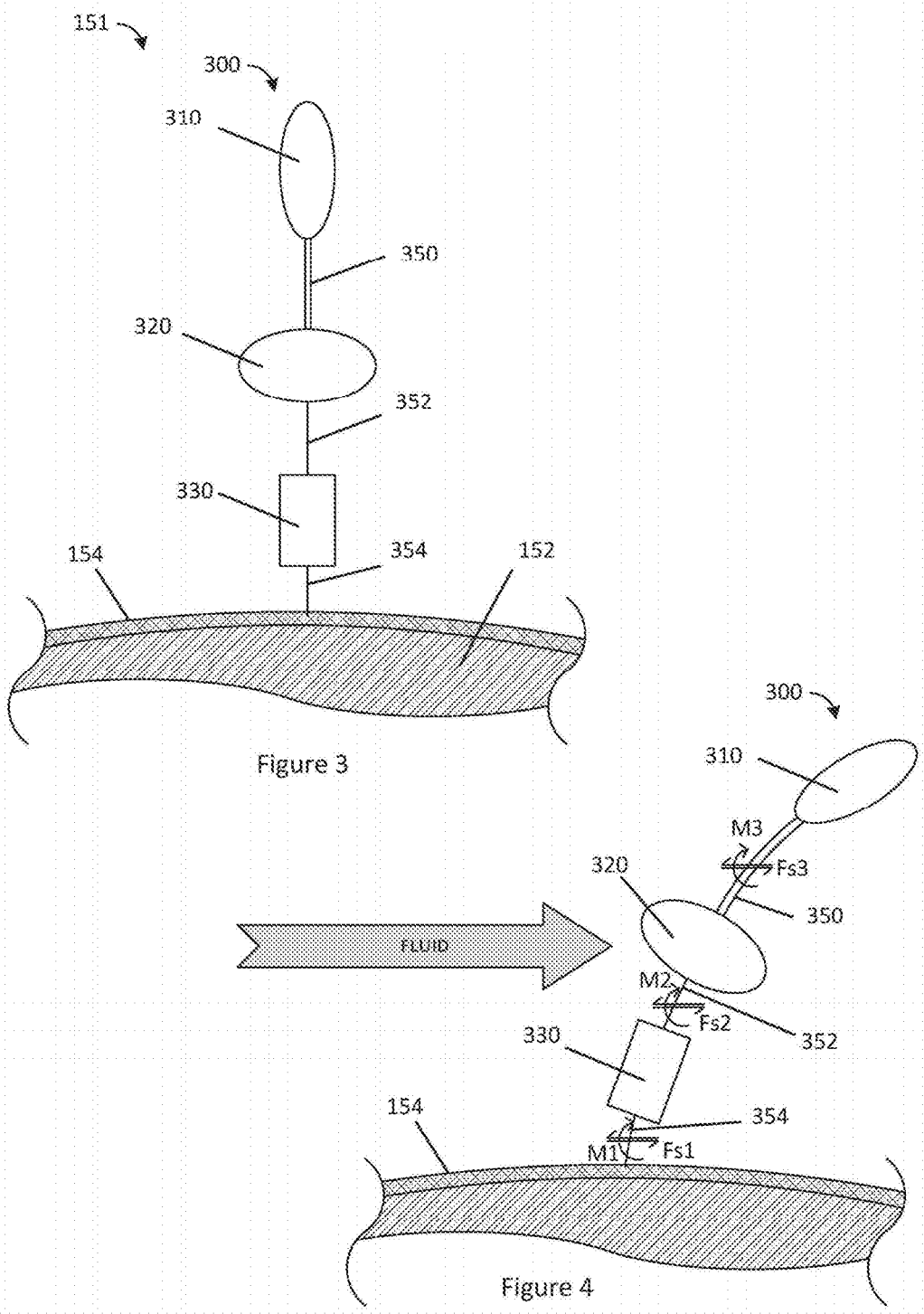
FIG. 3 depicts an exemplary schematic of a portion of an adsorbent comprising a ligand and a substrate.
FIG. 4 depicts a conceptual illustration of forces applied to an adsorbent by fluid flowing past a ligand.

FIG. 3 depicts an exemplary schematic of a portion of an adsorbent 151. In this example, the adsorbent 151 comprises a substrate 152 and a substrate surface 154. In certain embodiments, the substrate surface 154 is an oxidized form of the material forming the substrate 152. In other embodiments, the substrate surface 154 is absent and the material of the substrate 152 is exposed on the surface. In other embodiments, the substrate surface 154 is replaced by a coating that comprises a material different from the material of the substrate 152.

In certain embodiments, the substrate surface 154 is attached to a ligand that has been selected to bind to the target component to be removed from a fluid. In certain embodiments, the fluid is blood or a portion thereof such as plasma, the target component to be removed is a TNF receptor, and the ligand binds to a portion of the TNF receptor.

Dimensions of a column 100 may be based in part on selection of a path length (140 or 142 of FIG. 2) to provide a desired contact time between the fluid and the ligand. Given that there is a plurality of actual flow paths 142, each possibly having a different length, the actual contact time along each path 142 may correspondingly be different. The desired contact time is typically a minimum contact time. Use of the length of the idealized path 140 in conjunction with a flow rate and cross-sectional area will provide a minimum contact time for a column 100.

In certain embodiments, the ligand comprises one or more ligands 300 that are coupled to the substrate surface 154. In this example, the target component is a soluble TNF receptor and the ligand 300 comprises a TNFα trimer 310. In certain embodiments, the ligand 300 comprises a linker 320 coupled between the trimer 310 and the substrate surface 154. In certain embodiments, a functional group 330 may be disposed within the ligand 300.

In the example ligand 300 of FIG. 3, there is a bond 350 between the trimer 310 and the linker 320, a bond 352 between the linker 320 and the functional group 330, and a bond 354 between the functional group 330 and the surface coating 154. Some ligands may have additional internal structures while others may omit certain of these structures. This structure of ligand 300 is provided only as an example to illustrate the concept, which is not limited to a specific structure. In certain embodiments, bond 354 may be directly between linker 320 and surface coating 154. The bonds 350, 352, 354 may be single or double ionic or covalent bonds. Each of the bonds 350, 352, 354 has a bond strength, wherein applying a force that exceeds the bond strength will break the bond.

Bonds of different types have different strengths. Table 1 (Source: T. L. Cottrell, *The Strengths of Chemical Bonds*, 2d ed., Butterworth, London, 1958; B. deB. Darwent, *National Standard Reference Data Series*, National Bureau of Standards, no. 31, Washington, 1970; S. W. Benson, *J. Chem. Educ.* 42:502 (1965); and J. A. Kerr, *Chem. Rev.* 66:465 (1966)) lists selected values of bond strengths between various elements. The bond strength is affected by both the type of bond and the peripheral chemical structure in ways that may be unexpected. For example, line 1 of Table 1 shoes that a carbon-nitrogen bond has a bond strength that is larger than the strength of the same bond when the carbon has a second nitrogen attached and the nitrogen has an oxygen attached. Similarly, a double bond between carbon and oxygen (line 5) is weaker than a single bond (line 4). Accordingly, leaching cannot be predicted based upon bond strength alone.

TABLE 1

Bond Dissociation Energies

| Bond | $\Delta Hf_{298}$ (kJ/mol) |
|---|---|
| C—N | 770 |
| NC—NO | 121 |
| N—O | 630 |
| C—O | 1077 |
| C=O | 749 |
| OC=O | 532 |

Returning to FIG. 3, the strength of bond 354 may be a limiting aspect with respect to leaching of the ligand. Strengthening bond 354 may reduce leaching. In an example of strengthening the bond of a ligand to a substrate, a polysaccharide substrate is used and the surface of the substrate is oxidized, for example using an inorganic salt such as sodium metaperiodate ($NaIO_4$). The substrate is then exposed to the ligand, whereupon a primary amine of the ligand forms a Schiff base with the oxidized substrate surface layer. This is a relatively weak and reversible double bond. This bond is converted to a single non-reversable bond, for example an amine bond, by exposure to a mild reducing agent, for example sodium cyanoborohydride ($NaBH_3CN$).

FIG. 4 depicts a conceptual illustration of forces applied to the example ligand, i.e. ligand 300, by fluid flowing past the ligand 300, according to certain aspects of the present disclosure. The characteristics of the fluid flow depend upon numerous factors, for example the viscosity of the fluid, solid or semi-solid components suspended in the fluid, and adhesion between the fluid and the substrate surface 154. In certain embodiments, the flow of the fluid may be laminar, particularly immediately proximate to the substrate surface 154, with a velocity gradient related to distance from the substrate surface 154. In certain embodiments, the flow of the fluid may be partially turbulent.

Depending on the characteristics of the fluid flow, forces are applied to any of the structures of ligand 300, for example the trimer 310, the linker 320, or the functional group 330. These forces may then create shear forces and moments at the bonds of the ligand 300. In the conceptual structure of FIG. 4, shear forces Fs1 and moment M1 are created at bond 354, shear forces Fs2 and moment M2 are created at bond 352, and shear forces Fs3 and moment M3 are created at bond 350.

Figure 5A:
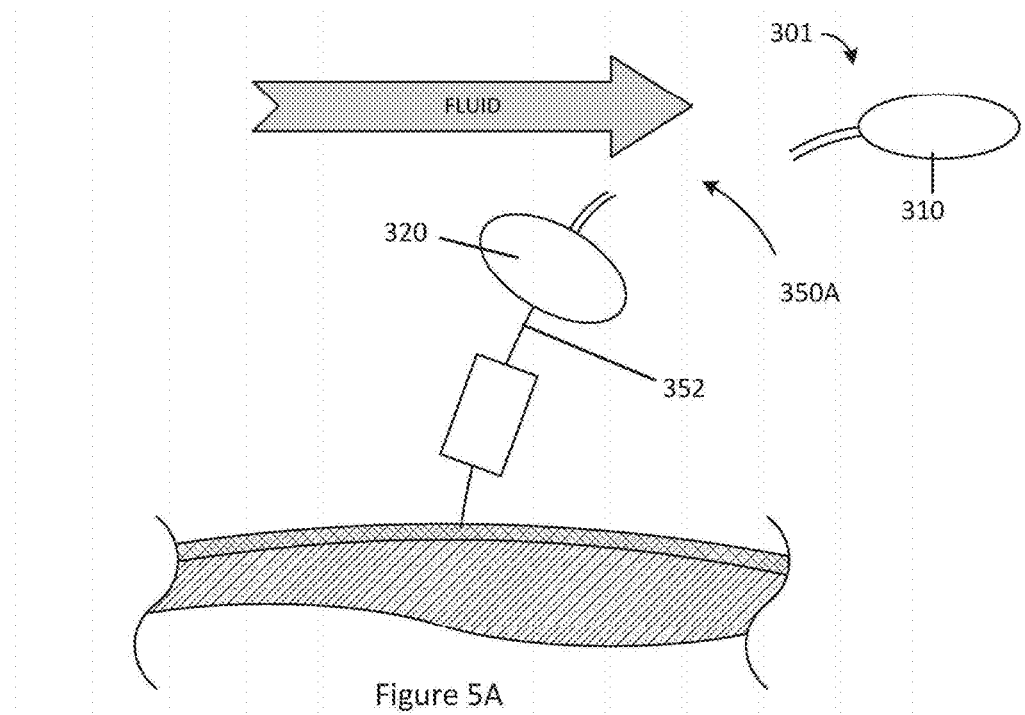
FIGS. 5A-5B depict conceptual illustrations of dissociation of ligand, or a portion thereof, from an adsorbent.

FIG. 5A depicts a conceptual illustration of breakage of an internal bond of ligand 300, according to certain aspects of the present disclosure. In this example, one of the shear forces Fs3 or moment M3, shown in FIG. 4, has created a stress in the bond 350 that exceeded the strength of that particular bond. When this occurred, the bond 350 "broke" and a ligand fragment 301, which comprises a portion of the trimer 310, became separated from the rest of ligand 300. In certain embodiments, the break 350A may be at the interface at the linker 320 while in other embodiments, the break may occur at the interface at the trimer 310 or at an intermediate location. In general, reducing the velocity of the fluid proximate to the example ligand (ligand 300) will reduce leaching of the ligand into the fluid.

In the case where shear forces Fs2 and M2 of FIG. 4 exceeded the strength of the bond 352 before the breakage of bond 350, then the bond 352 would have broken first. This would result in much the same situation, wherein the detached fragment 301 comprises a larger portion of the original ligand 300. In both cases, the detached portion 302 includes a portion of trimer 310.

Figure 5B:
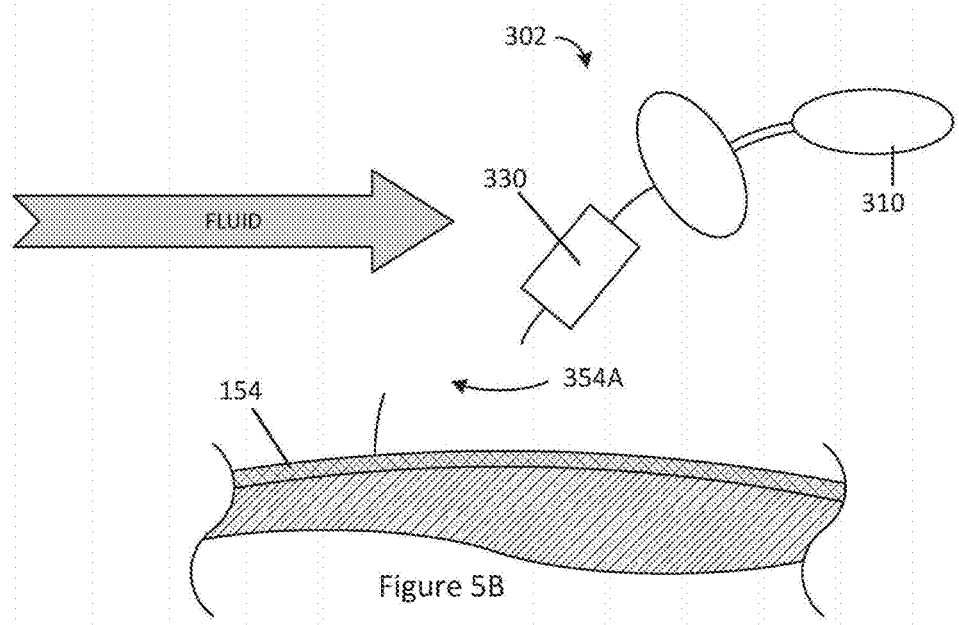

FIG. 5B depicts a conceptual illustration of breakage of the bond between ligand 300 and substrate surface 154, according to certain aspects of the present disclosure. In this example, the break 354A may be between the functional group 330 and the substrate surface 154. In other scenarios, a portion of the substrate surface 154 may have broken away from the remainder of the substrate surface 154 or a bond in the functional group 330 may be the point of separation. In all cases, the entire ligand 300 is considered to have become separated from the bead 150 as portion 302. In the case of the ligand 300 comprising TNF-alpha, the detached fragments 301, 302 may be considered scTNF-alpha.

Figure 6:
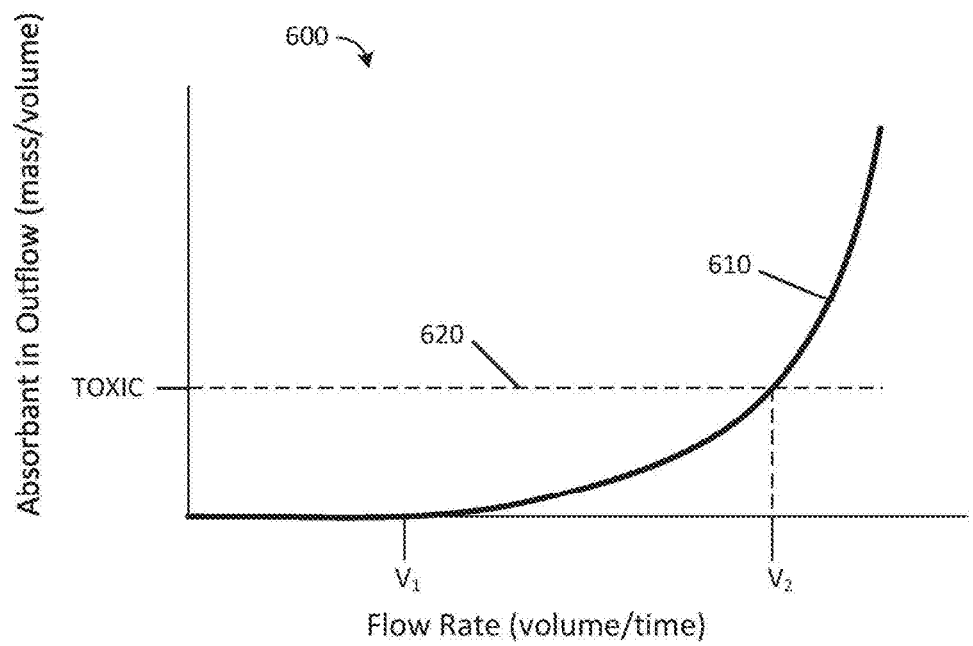
FIG. 6 depicts an illustrative plot of the steady-state amount of a ligand present in the outflow of a column.

FIG. 6 depicts an illustrative plot 600 of the steady-state amount of ligand present in the outflow, i.e. "leaching" from the column, based on the flowrate of liquid through a column, according to certain aspects of the present disclosure. This type of experimentation can be used to determine the particular design aspects of a column, for example the cross-sectional area of the compartment and the particle type, geometry and size (e.g., bead diameter). As the strength of the weakest bond of a ligand is dependent upon the structure of the ligand and how it is bound to the substrate and the local fluid velocities within the compartment vary depending on the type of substrate, there is no standard velocity threshold for detachment of ligand from the substrate. Determination of the amount of ligand in the outflow fluid may be determined using a suitable laboratory process, for example analytical chromatography, that is selected to detect a portion of the leached ligand. In the example ligand of FIG. 3, it is preferable to detect the trimer 310 as it will be present in any fragment of the ligand 300 that dissociates from the substrate 152.

Conceptually, and without being bound by theory, FIG. 6 illustrates a fluid that does not contain any of the ligand flowing into a column over a range of flow rates and the level of ligand is measured in the fluid flowing out of the column. Up to a flow rate of $V_1$, there is no measurable amount of ligand in the outflow fluid. Above that flowrate, the amount of ligand in the outflow starts to increase, indicating that the local fluid velocity at some location within the column compartment has surpassed a threshold at which the force created on one of the bonds of the ligand is exceeding the strength of that bond, thereby dissociating the ligand or ligand or a portion thereof from the substrate.

Conceptually, the amount of ligand in the outflow may increase at a linear or, as shown in FIG. 6, an exponential rate as the local fluid velocity exceeds the threshold in a growing volume of the compartment. In certain circumstances, there may be a discontinuity (not shown in FIG. 6) in the curve 610, for example caused by mechanical compression of the substrate that modifies the flow paths and creates higher local velocities at the same overall flow rate.

In this example, the amount of ligand that is present in the outflow fluid at or above a flow rate of $V_2$ is considered "toxic." An amount of ligand that is measurable while less than the toxic level, e.g. the amount present in the fluid at flow rates above $V_1$ while below $V_2$, may be acceptable. In certain embodiments, an acceptable predetermined level of ligand in the outflow fluid is selected.

Figure 7:
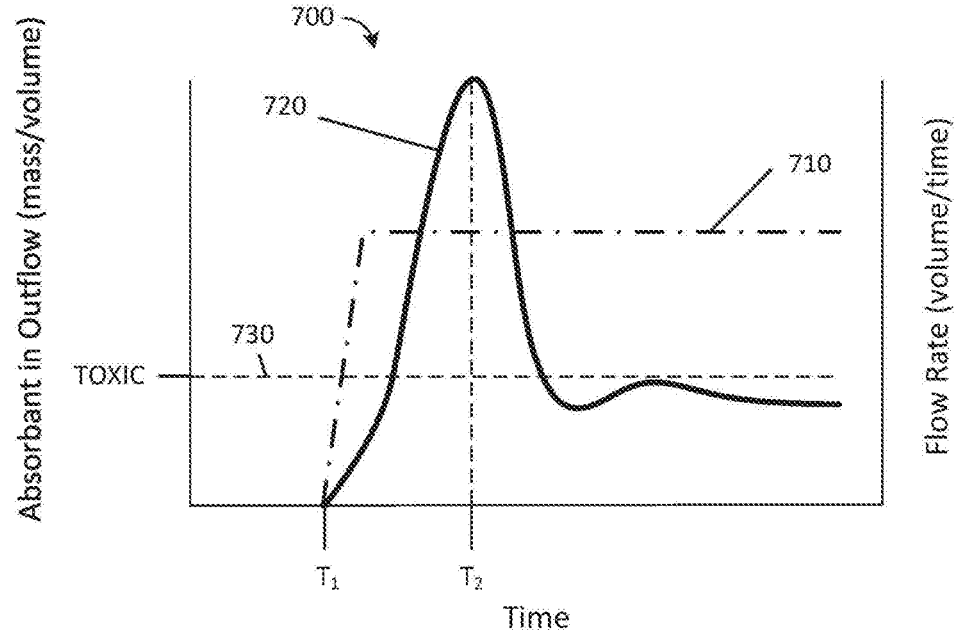
FIG. 7 depicts an illustrative plot of the amount of ligand present in the outflow of a column during start-up.

FIG. 7 depicts an illustrative plot 700 of the amount of ligand present in the outflow of a column during start-up, according to certain aspects of the present disclosure. Curve 710 depicts the flow rate through a column when a pump is started at time $T_1$. The pump of this example creates a near step-function flow rate profile with a steep rise to the target flow rate (the right y-axis). Even if the column is pre-filled with fluid, this flow profile may create a transient pressure wave within the column that may generate shear forces and moments on the ligand, as described with reference to FIG. 4, that are larger than the steady-state magnitudes. As such, the bond strengths of the ligand may be exceeded in a much larger portion of the compartment of the column than during steady-state flow, resulting in a surge of separated ligand fragments in the initial outflow as illustrated by curve 720. The amount of ligand in the outflow fluid is depicted in curve 720, which corresponds to the left y-axis) that peaks at time $T_2$ then decreases to a steady-state level commensurate with the steady-state flow rate of curve 710. In this example, the toxic level 730 is above the steady-state value but the surge of curve 720 exceeds the toxic value.

This surge effect can be avoided by controlling the acceleration of the pump to slowly rise to the target flow rate without a surge in level of ligand in the outflow. The acceptable rate of rise is dependent upon several factors, for instance the viscosity of the fluid, the pore size of the inlet and outlet, the column cross-sectional area, and the bead size. In certain embodiments, this surge may be acceptable if the initial fluid with the increased level of ligand is diverted and not returned to the patient.

Returning to a consideration of the column 100 of FIG. 1 in light of surges in pressure or flow upon start-up, certain features may be desirable to mitigate or avoid the effects. In certain embodiments, the inlet 130, and equivalently the outlet 134, may move with respect to the body 110 of column 100. In certain embodiments, a spring (not shown in FIG. 1) applies a bias force to the inlet 130. In certain embodiments, there is a sliding seal between the perimeter of the inlet 130 and the interior wall of the body 110 that prevents fluid from bypassing the inlet 130. In certain embodiments, there are channels (not shown in FIG. 1) proximate to the perimeter seal of the inlet 130 that are uncovered by displacement of the inlet 130 with respect to the body 110, thereby allow bypass flow of fluid around the inlet 130. This bypass flow may reduce an in-rush pressure surge, which is discussed further with respect to FIG. 7.

In certain embodiments, the direction of fluid flow through the compartment 120 is "up," i.e. opposes gravity, and the flowing fluid may cause a portion of the beads 150 of FIG. 2 to separate from each other, e.g. "float." A sufficient bias force applied to the outlet 134 may prevent this separation and facilitate proper operation of the column 100 in the "inverted" position.

In certain embodiments, a surge of fluid during start-up may create a pressure wave in the compartment 120 that compresses the beads 150 of FIG. 2, causing a permanent degradation in the performance of the column 100. Movement of the inlet 130 in the direct of flow may bring the inlet 130 into contact with a flow control (not shown in FIG. 1) that masks a portion of the porous area of the inlet 130 such that flow through the inlet 130 is restricted. In the case of a surge in initial flow rate, this restriction may restrict the rate of rise of the fluid velocity within the compartment 120, thereby avoiding compression of the beads 150. Alternately, movement of the outlet 134 in the direction of flow may avoid compression of the beads by allowing separation of the beads 150 during the pressure surge. In both cases, a spring returns the inlet 130 or outlet 134 to the original position after the pressure surge dissipates.

FIG. 8A depicts a schematic example of a ligand 800 comprising a trimer 810, according to certain aspects of this disclosure. The trimer 810 has three monomers 812 of an organic structure, for example TNF-alpha, arranged proximate to each other. Each monomer 812 comprises one or more sites having a structure that will couple to a portion of a target component of a fluid, for example TNFR1 in blood plasma, that is proximate to the monomer 812. The monomer 812A is coupled to a substrate 830 by a linker structure 832 that forms a chemical bond, for example an ionic or covalent bond, to each of the monomer 812A and substrate 832. Monomers 812B and 812C are coupled to monomer 812A through an electromagnetic attraction, for example van der Waals force or a hydrogen bond. Unlike ionic or covalent bonds, electromagnetic attractions do not result from a chemical bond and are comparatively weak and therefore more susceptible to disturbance. Consequently, monomers 812B and 812C can be separated from monomer 812A at a lower level of applied force than is required to separate monomer 812A from the substrate 832.

FIG. 8B depicts a schematic example of a ligand 850 comprising a trimer 860, according to certain aspects of this disclosure. The trimer 860 has three monomers 812 of an organic structure, for example TNF-alpha, that are coupled to each other via linkers 833 to form a single chain structure that is coupled to a substrate 830 by a linker structure 832 at one end of one of the monomers 812. As the linkers 832, 833 form chemical bonds to the structures on each side, it requires a higher level of applied force to detach any portion of ligand 860, for example one of the monomers 812, from the substrate 830 than is required to separate a portion of ligand 800, for example monomers 812B or 812C, from substrate 830. Forming the trimer 860 in this form thus provides an increased resistance to leaching of a portion of the ligand 850 into fluid passing proximate to the substrate 832, compared to leaching of a portion of the ligand 800 under the same conditions, e.g. fluid viscosity and relative velocity, temperature, substrate composition, and monomer structure.

FIG. 9 depicts a 2-stage column 900, according to certain aspects of this disclosure. In certain embodiments, the first stage 901 is generally the column of FIG. 1, with a housing 110, compartment 120 containing a first substrate 910, for example a ligand that will capture a component of fluid flowing into entrance port 132. The exit port 136 is coupled to the entrance port 132B of a second stage 902, which has a compartment 120B containing a second substrate 920 having a second effect, for example capture of fragments of the ligand that are separated from the substrate 910. The second stage 902 is intended to reduce the risk of the ligand of substrate 910 being present in the fluid flowing out of the exit port 136B.

Table 2 (Source: G. T. Hermanson et al., Immobilized Affinity Ligand Techniques, Academic Press, Inc., 1992 Harcourt Brace & Company) lists the leakage, or "leaching," of an antibody Immunoglobulin G (IgG) that was attached to a support comprising agarose, a polysaccharide polymer frequently used in molecular biology for the separation of large molecules by electrophoresis. The IgG was tagged with iodine-125 ($^{125}$I), which is a radioisotope commonly used for tagging antibodies in radioimmunoassay and other gamma-counting procedures involving proteins outside the body. The tagged IgG was attached to the agarose using different methods, such as described in FIGS. 10A-10D. The initial amount of radioactivity, measured in counts per minute (cpm), was measured for specimen and the IgG that leached from the substrate over a 28-day period, then compared to provide a standardized comparison.

orders of magnitude) reduction in leaching observed in the data of FIGS. 14A-14B and discussed further below.

Figure 10A:
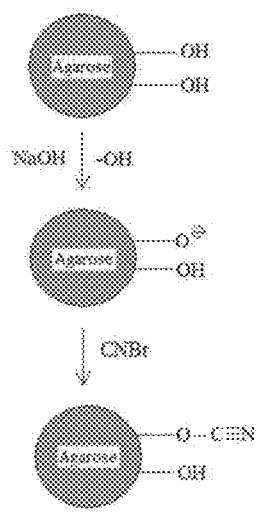
FIG. 10A depicts a process wherein cyanogen bromide is used to prepare an agarose substrate.

FIG. 10A depicts a process wherein cyanogen bromide (CNBr) is used to prepare an agarose substrate, according to certain aspects of this disclosure. The agarose is exposed to sodium hydroxide (NaOH) that reacts with the hydroxl groups on the agarose to form cyanate esters M—O—C≡NC. Although not wishing to be bound by any particular theory, it may be that forming a Schiff base and then converting with reductive amination by treating with sodium cyano borohydride produces a higher strength bond.

Figure 10B:
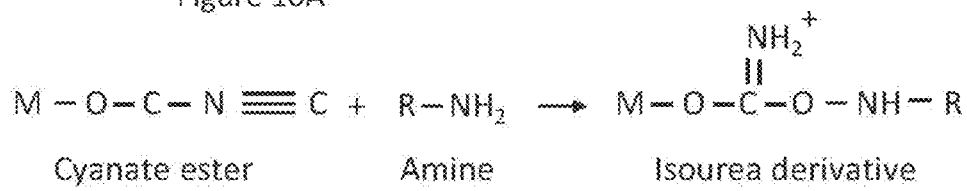
FIG. 10B is a chemical equation for reacting cyanate esters formed by CNBr with an amine R—NH2 to attach a ligand to agarose.

FIG. 10B is a chemical equation for reacting the cyanate esters formed by CNBr with an amine R—NH$_2$ to attach a protein ligand to the agarose by forming an isourea derivative, which is related to the first entry of Table 2.

Figure 10C:
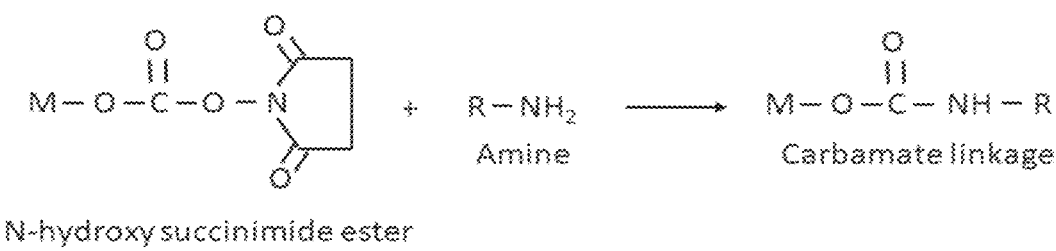
FIG. 10C is a chemical equation for attaching a ligand to agarose previously activated with N-hydroxyl succinimide (NHS).

FIG. 10C is the chemical equation for attaching a protein ligand to the agarose previously activated with N-hydroxyl succinimide (NHS) by forming an amine bond to the NHS ester, which is related to the fourth entry of Table 2.

Figure 10D:
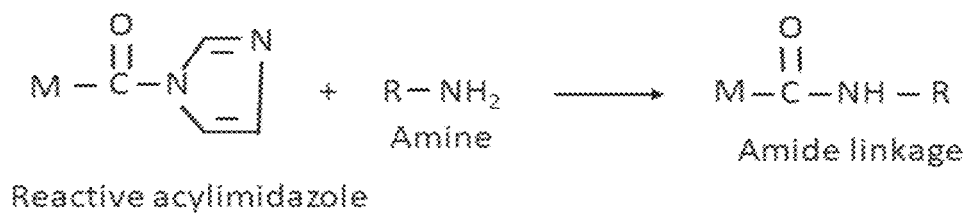
FIG. 10D is a chemical equation for attaching a ligand to agarose by forming an amine bond to an acylimidazole previously formed on the surface of the agarose.

FIG. 10D is the chemical equation for attaching a protein ligand to the agarose by forming an amide bond to the acylimidazole previously formed on the surface of the agarose.

Figure 11:
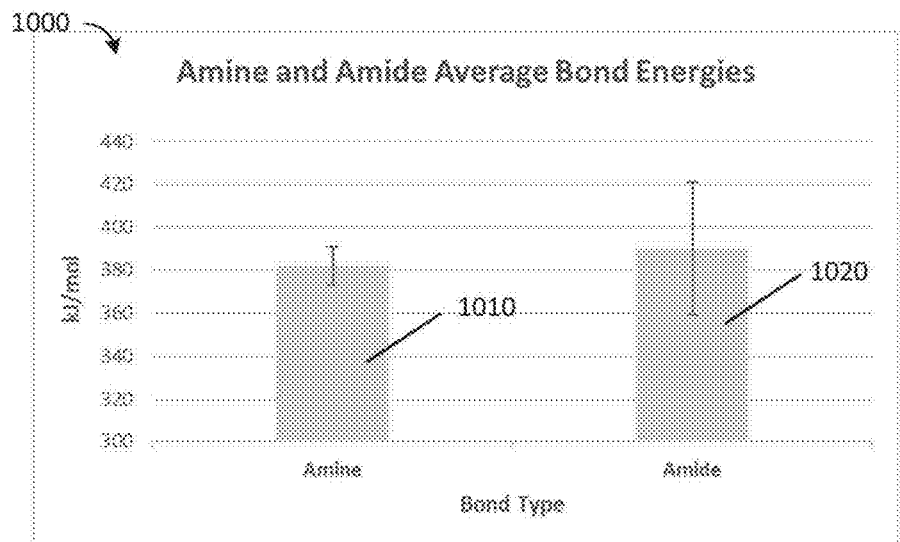
FIG. 11 is a bar graph showing bond energies of two basic types of biochemical bonding chemistries.

FIG. 11 is a plot 1000 of the bond energies, measured in kiljoules per mol (kJ/mol), of two basic types of biochemical bonding chemistries—amines and amides, according to certain aspects of this disclosure. The data is from I. I. Marochkin et al., Amide bond dissociation enthalpies: Effect of substitution on NAC bond strength, *Comp and Theo Chem* 991 (2012) 182-191, and J. Lalevée et al., N—H and r(C—H) Bond Dissociation Enthalpies of Aliphatic Amines, *J. Am. Chem. Soc.* 2002, 124, 9613-9621. While the average bond energy of an amine is lower than the bond energy of an amide, the scatter 1020 of the amide is much wider than the scatter 1010 of the amine. As a result, one would not expect the actual bond energy of the two chemistries to be different.

Based on the existing laboratory data, examples of which are provided in Table 1 and FIG. 11, it is not possible to predict the strength of an attachment of a ligand to a

TABLE 2

Leakage of $^{125}$I Labeled IgG from Immobilized IgG Affinity Supports Prepared by Various Coupling Methods

| Support | Total Radioactivity in 1 ml of gel (cpm) | Total counts leaked in 28 days (cpm) | Leakage per day (%) | Bond |
|---|---|---|---|---|
| CNBr-agarose | 6.20 × 10$^4$ | 57800 | 0.03 | —O—C(NH2$^+$)—O—NH—R |
| CDI-agarose | 0.47 × 10$^4$ | 4948 | 0.04 | —O—C(O)—NH—R |
| Tresyl-agarose | 0.43 × 10$^4$ | 26306 | 0.22 | —O—C(O)—NH—R |
| NHS-activated | 0.62 × 10$^4$ | 74846 | 0.43 | —C(O)—NH—R |
| Periodate/Reductive amination | 1.00 × 10$^4$ | 6948 | 0.02 | —CH2—NH—R |

\*\* "R" as used in Table 2 is a protein or polypeptide.

It can be seen from Table 2 that the standardized leakage varies over an order of magnitude across the various methods of attaching a ligand to a substrate using an amine. The first entry in the table is related to the process depicted in FIGS. 10A-10B. The leakage rates of CNBr-agarose, CDI-agarose, and Reductive amination are all similar, especially when considering that these are experimental measurements that intrinsically have standard deviation ranges. Based on this type of bench characterization, the small differences between bond types does not predict that reductive amination would create significantly less leaching than the other methods of attachment. This contrasts with the large (2 substrate based on the chemistry or preparation sequence. Based on the textbook data of FIG. 11, one would expect an amine bond to be weaker than an amide bond.

Figure 12:
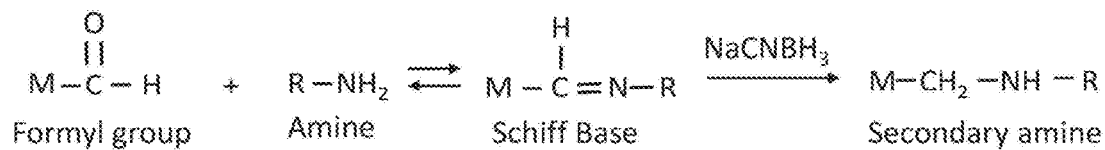
FIG. 12 is an exemplary chemical equation for attaching a primary amine of a ligand to a substrate using sodium cyanoborohydride ($NaCNBH_3$).

FIG. 12 is an exemplary chemical equation for attaching a protein ligand to a substrate, according to certain aspects of this disclosure. A substrate surface, for example comprising a polysaccharide, has been oxidized to create formyl groups on the surface of the substrate. Exposure to a primary amine creates a Schiff Base on the surface, which is easily reversible and therefore unsuitable as a nondetachable bond to the substrate. Subsequent exposure to sodium cyanoborohydride (NaBH₃CN or NaCNBH₃) converts the Schiff Base to a strong non-reversible secondary amine bond.

Figure 13:
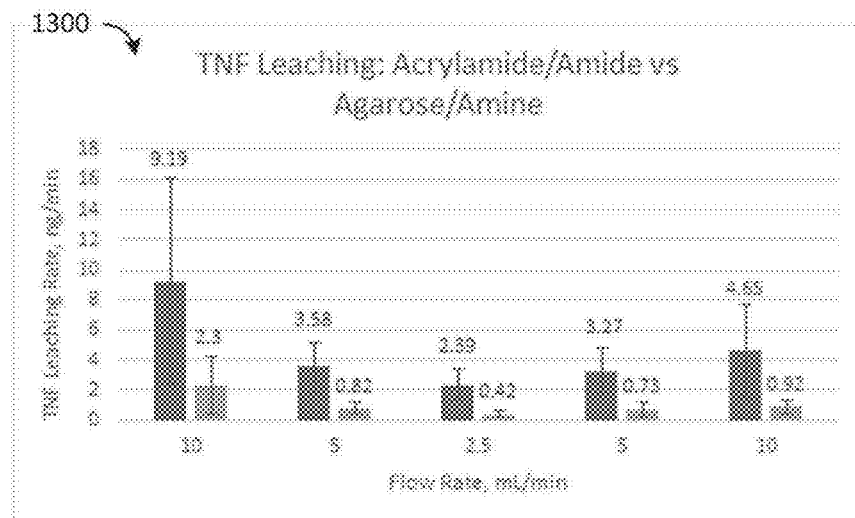
FIG. 13 depicts an exemplary comparison of the bench-test of leaching rates of a TNF ligand attached to an acrylamide substrate by an amide bond (left bar of each pair) and a TNF ligand attached to an agarose substrate by an amine bond (right bar of each pair). The difference between acrylamide and agarose leaching rates for each flow rate was significant ($p<0.05$).

FIG. 13 depicts an exemplary comparison 1300 of the bench-test leach rates of two combinations of substrate and bond type, according to certain aspects of this disclosure. The left set of columns are measurements taken with a column using acrylamide beads with amide bonds attaching the TNF-alpha ligands to the beads. The right set of columns are measurements taken from the same column using agarose beads with amine bonds attaching the TNF-alpha ligands to the beads, such as formed by the equation of FIG. 12. The "whisker" bars represent the statistical scatter of the multiple measurements of the data set of the respective columns. It can be seen that, contrary to the trend suggested by FIG. 11, the amine bonds allow less leaching, i.e. have formed stronger attachment of the ligands to the substrate. It has not escaped our attention that multiple linkages to individual polypeptides may increase the overall bond strength, the said polypeptide having distributed two or more linkages to the substrate surface. This possibility is reduced in the example since the overall capacity exceeds the molar amount of bound ligand by seven-fold (data not shown) with amine linkages and by comparison by 10 fold with amide linkages. Thus the ligand density in each case is less than the available active sites by a substantial margin. The difference between the two systems is statistically significant for all of the flow rates ($p<0.05$). The leaching was measured at various flow rates, showing a distinct reduction in the leaching rate at lower flow rates for both combinations of bond type and substrate.

Figure 14:
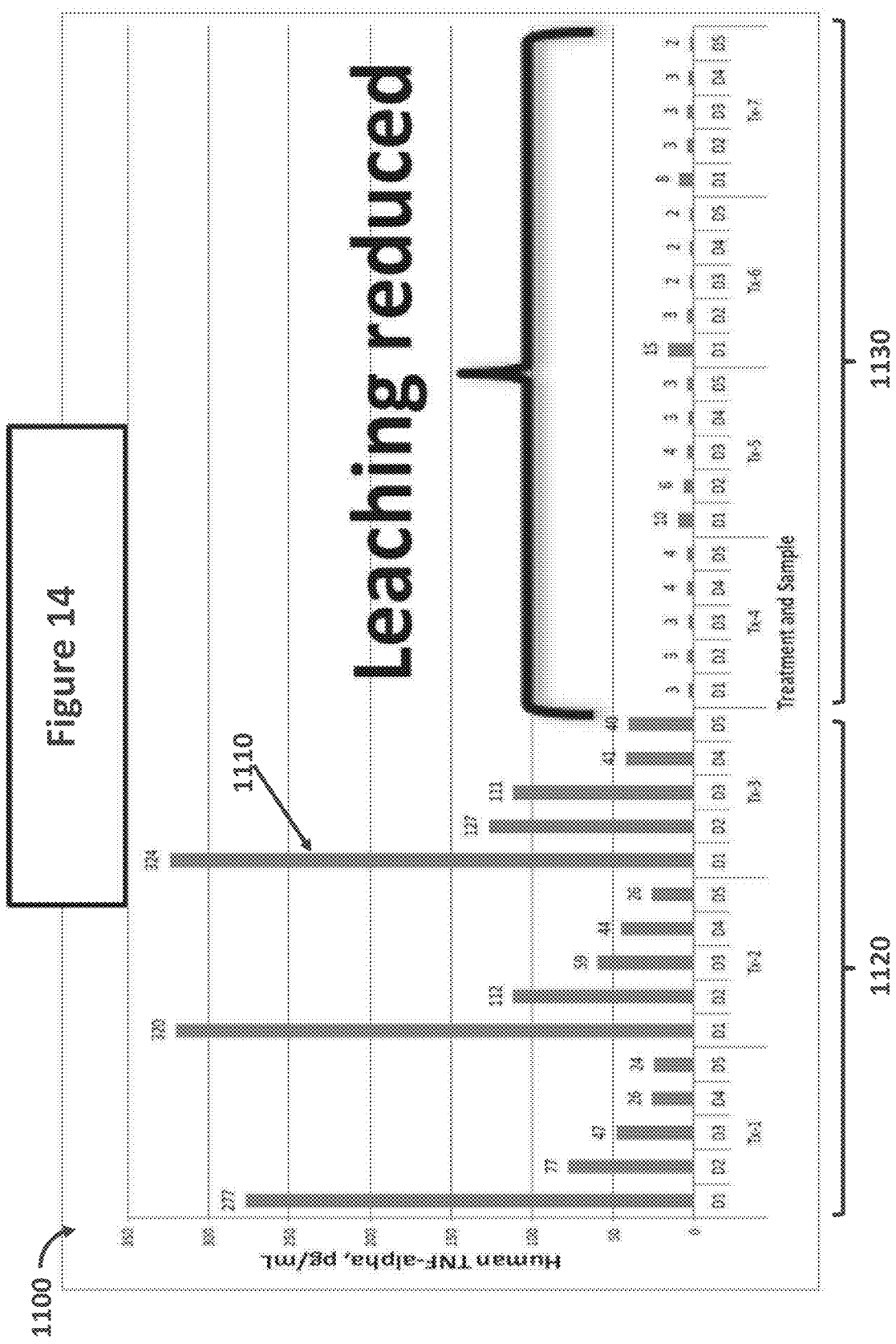
FIG. 14A depicts a plot of experimental data comparing leaching of a single chain TNF ligand (scTNF) attached to a substrate with an amide bond (Tx1, Tx2 and Tx3)
FIG. 14B depicts a scTNF ligand attached to a substrate with an amine bond (Tx4, Tx5, Tx6 and Tx7).

FIGS. 14A-14B depicts a plot 1100 of experimental data comparing leaching of two systems, according to certain aspects of this disclosure. A treatment to remove sTNF-R was repeatedly administered in six sequential sessions on a single patient, with the session data being indicated by groups Tx1-Tx6 in temporal order. The treatment used TNF-alpha as a ligand in a column as disclosed herein, and therefore scTNF-alpha in the outflow is an indication of leaching. During each session, the level of scTNF-alpha in the processed plasma (the outflow from the column), was sampled at 30-minute intervals (5 times per treatment) and measured and plotted as columns 1110. The first three sessions (Tx1-Tx3) in group 1120 were conducted with a column system A that comprises a ligand bound to a substrate with an amide bond. It can be seen that the initial level (D1) of scTNF-alpha in the outflow during Tx1-Tx3 is in the range of 250-350 picograms per microliter (pg/ml) with subsequent levels decreasing in a monotonic manner over the course of each treatment to a final level in the range of 20-40 mg/pl. Sessions Tx4-Tx7 of group 1130 were conducted with a column system B as described herein, wherein system B included a substrate having an oxidized surface and the same ligand bound to the substrate with a non-reversible secondary amine bond. All five of the measurements of scTNF-alpha in the outflow of each session Tx4-Tx7 are below 20 pg/ml, with most being below 5 pg/ml.

Figure 15:
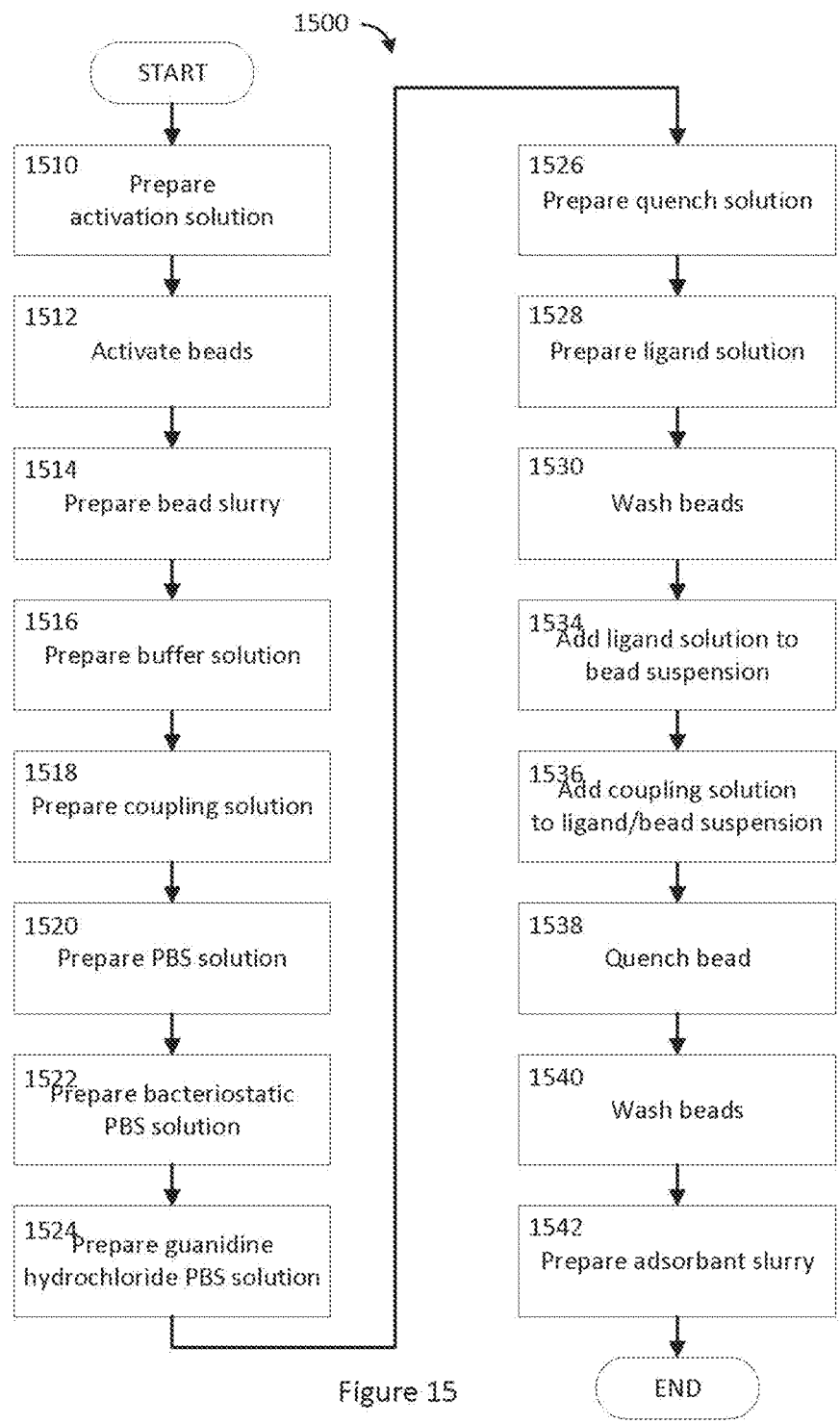
FIG. 15 depicts a flowchart of an exemplary process 1500 for preparing an adsorbant, according to certain aspects of this disclosure.

FIG. 15 depicts a flowchart of an exemplary process 1500 for preparing an adsorbant, according to certain aspects of this disclosure. One of ordinary skill in the art will recognize that certain aspects of the process may be modified or re-arranged without departing from the concept as presented.

Activation of Substrate: An activation solution is prepared in step 1510 by adding water to sodium metaperiodate. In certain embodiments, approximately 42.8 g of sodium metaperiodate is added to a flask and then 1 liter of distilled water is added to the flask to make the activating solution.

The substrate is activated in step 1512 by first washing the substrate with water. In certain embodiments, the substrate comprises polysaccharide beads, as will be referenced in the remaining steps of this example process. In certain embodiments, the beads comprise a linear polymer comprising disaccharides such as agarose. In certain embodiments, the beads comprise Sepharose 6 Fast Flow Beads from Cytiva. In certain embodiments, the beads are washed 6 times with 1 bed volume of sterile water, aspirating each wash. The activation solution is then added to the washed beads to resuspend the aspirated beads. In certain embodiments, one bed volume of activation solution is added to one bed volume of beads. In certain embodiments, the beads are then shaken for 90 minutes. The liquid is aspirated, and the beads are then washed again with water. In certain embodiments, the beads are washed 6 times with 1 bed volume of water, aspirating each wash.

A bead slurry is prepared in step 1514 by adding an ethanol solution to the aspirated beads. In certain embodiments, the ethanol solution is approximately 20% ethanol. In certain embodiments, the amount of ethanol solution added is sufficient to create a 50% slurry. The bead slurry can be stored at 2-8° C.

Preparation of Process Solutions: A buffer solution is prepared in step 1516 adding MOPS (3-(N-morpholino) propanesulfonic acid) sodium salt ($C_7H_{14}NNaO_4S$ MW 231.25) to water. In certain embodiments, approximately 23 g of MOPS sodium salt is added to 900 milliliters of sterile water to make the buffer solution. In certain embodiments, this creates a 0.1M MOPS buffer solution with a pH of approximately 10. The pH can be adjusted by addition of hydrochloric acid. The volume is then adjusted to 1 liter. In certain embodiments, the buffer solution has a pH in the range of 8.5-10. In certain embodiments, the buffer solution has a pH=8.8.

A coupling solution is prepared in step 1518 by adding sodium cyanoborohydride (NaCNBH₃) to the buffer solution of step 1516. In certain embodiments, approximately 63 g of sodium cyanoborohydride is added to 1 liter of the buffer solution. In certain embodiments, the final pH is 8.5-10.

Sodium cyanoborohydride is used to reduce the Schiff base without affecting the aldehyde groups of the oxidized agarose. The pH of the sodium cyanoborohydride coupling solution is intentionally kept in the range of 8.5-10 to avoid reactivities other than with free lysines of the ligand which would affect the integrity of the substrate, which preferentially forms the desired secondary amine bonds when at a pH of 8.5-11. The ligand solution created in step 1528 has a pH of 8.5-10 and using a coupling solution having a pH that is lower than 8.5 would reduce the pH of the mixture and may interfere with the formation of secondary amine bonds and induce undesirable thioether linkages.

A PBS (phosphate-buffered saline) solution is prepared in step 1520 by adding sodium phosphate and NaCl to water. In certain embodiments, the PBS solution comprises 0.1M sodium phosphate and 0.15M NaCl and has an approximate pH of 7.1-7.3.

A bacteriostatic PBS solution is prepared in step 1522 by adding benzyl alcohol to the PBS prepared in step 5120. In certain embodiments, approximately 8.6 mL of benzyl alcohol is added to the PBS.

A guanidine hydrochloride PBS solution is prepared in step 1524 by adding guanidine hydrochloride to the PBS prepared in step 5120. In certain embodiments, approximately 334 g of guanidine hydrochloride is added to 1 liter of PBS. In certain embodiments, the solution is a 3.5M guanidine hydrochloride PBS solution.

A quench solution is prepared in step 1526 by adding ethanolamine hydrochloride ($C_2H_7NO$—HCL MW 97.54) to water. In certain embodiments, approximately 292.7 g of ethanolamine hydrochloride is added to 1 liter of sterile water. In certain embodiments, the solution is titrated with ethanolamine (liquid MW 61.08) to a pH of 8.9-9.1. In certain embodiments, the solution is a 3M ethanolamine quench solution.

A ligand solution is prepared in step 1528 by adding TNF to the buffer solution of step 1516 to create a solution having 1 mg/ml of TNF. In certain embodiments, the pH of the ligand solution is in the range of 8.5-10.0. In certain embodiments, the pH of the ligand solution is approximately 8.8. In certain embodiments, the TNF comprises scTNF. In certain embodiments, the ligand solution containing an amount of TNF that will be equivalent to 1 mg/mL of bead bed when 1 bed volume of the ligand solution is added to 1 bed volume of beads.

The pH of the ligand solution was chosen to avoid undesirable linkages in binding the ligand to the beads. The beads may comprise amino, thiol, or hydroxyl groups. Coupling to each of these groups is pH dependent:

1. For coupling thiol groups: pH 7.5-8.5 (forms thioether linkage)
2. For coupling amino groups: pH 8.5-11 (forms stable secondary amine linkage)
3. For coupling hydroxyl groups: pH 12 (forms ether linkage).

The ligand coupling was performed at a pH in the range of 8.5-10 to avoid side reactions with thiol groups at pH<8.5 and coupling to hydroxyl groups at pH 12. Within this range, pH=8.8 was selected as a nominal process value. This range avoids side reactions that would result in thioether or ether linkages. The pH range of 8.5-10 for the coupling process was selected.

Preparation of Adsorbant Beads: The liquid of the bead slurry of step 1514 is aspirated step 1530 and the beads are then washed with buffer solution of step 1516. In certain embodiments, the beads are washed 3 times with one bed volume of buffer solution, aspirating each wash.

The ligand solution of step 1528 is added to the aspirated beads to form a bead suspension in step 1534. In certain embodiments, 1 bed volume of ligand solution is added to 1 bed volume of beads. In certain embodiments, the resulting ligand/bead suspension is shaken for 10 minutes.

The bond between the ligand and the bead is strengthened in step 1536 by adding the coupling solution of step 1518 to the ligand/bead suspension. In certain embodiments, ⅕ bed volume of the coupling solution is added. In certain embodiments, the resulting mixture is shaken for 4 hours.

The beads are optionally quenched in step 1538 by aspirating the liquid from the mixture created in step 1536. The quench solution of step 1524 is then added to the beads. In certain embodiments, 1 bed volume of quench solution is added to 1 bed volume of beads. In certain embodiments an amount of coupling buffer of step 1518 equivalent to ⅕ of the quench solution volume is added. In certain embodiments, the resulting mixture is shaken for 1 hour.

Quenching eliminates the presence of unreacted carbonyl groups by reacting them with another small molecule containing a free amine group such as ethanolamine or ethylene diamine. When the carbonyl groups are reacted, this avoids the formation of Schiff base bonds with other proteins that may be present when the column is utilized for affinity chromatography capture of the target molecule in plasma. If quenching is not performed, proteins in the blood, such as albumin (55%), immunoglobulins (38%), and fibrinogen (7%) which together comprise nearly 100% of the free total protein in the blood, may bind to the unreacted carbonyl groups during treatment. This is not considered detrimental to the functionality of the capture ligands and, in fact, creates a biocompatible coating on the remaining surface of the bead that is formed from the patient's own protein. Given the large amount of albumin and other proteins in the blood, the unreacted carbonyl groups will be fully occupied by a very small fraction of them (less than 0.5% of the total blood protein for an unquenched device) within a few minutes of apheresis treatment with a negligible effect on the patient.

In contrast, the use of sodium borohydride to remove the carbonyl groups risks deleterious reactions that may occur on the ligand itself. As sodium borohydride is a powerful reducing agent, its use can disrupt the cystine bonds of TNF or other ligands.

The beads are washed in step 1540 with the guanidine hydrochloride PBS solution of step 1524. In certain embodiments, the beads are washed 8 times with 1 bed volume of guanidine hydrochloride PBS solution, aspirating each wash. The beads are then washed with PBS. In certain embodiments, the beads are washed 3 times with 1 bed volumes of PBS of step 1520, aspirating each wash. The beads are then washed with bacteriostatic PBS of step 1522. In certain embodiments, the beads are washed 3 times with 1 bed volume of bacteriostatic PBS of 1522, aspirating each wash.

Washing with the guanidine hydrochloride PBS solution removes the TNF that is not coupled with a strong secondary amine bond to the substrate, thereby reducing the amount of TNF that is available to leach out during apheresis treatment. As TNF is toxic, leaching of the TNF has been a major obstacle for previous attempts to use TNF as a capture ligand for clinical treatment. A guanidine hydrochloride PBS solution will similarly flush out the unbound molecules of other capture ligands and, again, reduce the leaching of the capture ligand during clinical treatment of a patient.

An adsorbant slurry is prepared in step 1542 by adding sufficient bacteriostatic PBS of step 1522 to the washed beads to make a 50% slurry. The adsorbant slurry can be stored 2-8° C.

A leaching rate is the amount of ligand that dissociates from a substrate over a period of time, when a blood component is flowed through a column comprising a adsorbent. A leaching rate is often determined by the amount of ligand detected in a column flow-through after a period of time. An initial leaching rate is a leaching rate measured after first contact of a ligand with a blood product for a predetermined period of time (e.g., 1 to 10 minutes) at a predetermined flow rate (e.g., 10 ml/minute). A leaching rate can be measured using a suitable apheresis system comprising a column comprising a ligand, where a patient's blood or blood component (e.g., plasma or serum) is flowed through the column. A leaching rate or initial leaching rate can be determined using a suitable method of detection.

In certain embodiments, a adsorbent comprises a ligand that is resistant to dissociation from a substrate surface. Dissociation of a ligand from a substrate can be determined by measuring a leaching rate, or initial leaching rate. In certain embodiments, a ligand comprises a bond that attaches a ligand to a substrate (e.g., amine bond). In certain embodiments, a ligand comprises a linker that attaches a ligand to a substrate. In some embodiments, a ligand that is attached to a substrate by an amine bond, or by a linker comprising an amine bond, is more resistant to dissociation than a ligand that is attached to a substrate by another type of bond. In certain embodiments, a ligand is at least 2-fold, at least 5-fold or at least 10-fold more resistant to dissociation from a substrate relative to the same ligand that is attached to the same substrate by a bond selected from an amide bond, a double bond, a triple bond, NC—NO, C—O, C=O, OC=O, OC—N, N—N, N=N, S—S, the like or combinations thereof. In certain embodiments, a ligand is at least 2-fold, at least 5-fold or at least 10-fold more resistant to dissociation from a substrate relative to another ligand comprising the same ligand that is attached to the same substrate by an amide bond or by a linker comprising an amide bond.

In certain embodiments, a ligand described herein displays an initial leaching rate of the ligand from the substrate of less than about 50 pg/ml, less than about 10 pg/min, less than about 7 pg/ml, less than about 5 pg/min, or less than about 2 pg/ml at a flow rate of 10 ml/min. In some embodiments, a ligand described herein displays an initial leaching rate of the ligand from the substrate of less than about 50 pg/ml, less than about 25 pg/ml, less than about 20 pg/ml, less than about 10 pg/ml, or less than about 5 pg/ml when measured at a flow rate of 10 ml/min for a period of time of about 1 to 10 minutes, 1 to 5 minutes or about 2-3 minutes.

The disclosed examples of a blood-filtering column are presented in the context of treating a patient by removal of a specific blood component, for example sTNF-Rs, from the blood, thereby enabling the patient's immune system to recognize and attack certain tumors that are masked by sTNF-Rs. The previously limiting side effect of leaching of the ligand, particularly the TNF-alpha of this example, are prevented by careful control of the fluid velocity within the column to avoid mechanical damage to the ligand. With the elimination of this legacy risk, use of this form of apheresis becomes a viable and safe method of treating conditions that have proven intractable with other therapies.

This application includes description that is provided to enable a person of ordinary skill in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. It is understood that the specific order or hierarchy of steps or blocks in the processes disclosed is an illustration of exemplary approaches. Based upon design preferences, it is understood that the specific order or hierarchy of steps or blocks in the processes may be rearranged. The accompanying method claims present elements of the various steps in a sample order, and are not meant to be limited to the specific order or hierarchy presented. Thus, the claims are not intended to be limited to the aspects shown herein, but is to be accorded the full scope consistent with the language claims.

Exemplary Embodiments

In an embodiment, a column has a compartment with a cross-sectional area, a bead having a diameter and disposed within the compartment, and a ligand coupled to the bead and selected to bind to the component. The cross-sectional area and bead diameter are selected to maintain a flow velocity of the fluid within the compartment below a first threshold. The ligand may comprise a ligand, wherein the ligand may comprise TNF-alpha, or portions or functional fragments or functional variants thereof, or a trimer of the TNF-alpha. The first threshold may be selected so as to maintain an amount of the ligand in the fluid flowing out of the outlet below a predetermined level. The first threshold may be selected so as to maintain a force applied by the fluid to the ligand below a second threshold, thereby reducing leaching of the ligand into the fluid. The ligand may comprise a bond having a strength and maintaining the force below the second threshold may avoid breaking the bond. The bead may comprise agarose and the bond may comprise an amine bond. The force may comprise one or more of a shear force and a moment and the second threshold may comprise one or more of a third threshold related to the shear force and a fourth threshold related to the moment. The compartment may further comprise an inlet, an outlet, and a flow path from the inlet to the outlet, wherein the flow path may have a length that may be selected to provide a contact time between the fluid and the ligand. The bead may comprise a plurality of beads. The ligand may comprise a plurality of portions of ligand respectively coupled to each of the plurality of beads. The ligand may be non-detachably coupled to the beads.

In an embodiment, a method includes one or more of the steps of receiving blood from the patient, separating the blood into at least two blood components, passing a portion of one of the blood components through a compartment having a cross sectional area and containing a plurality of beads having a diameter and to which are coupled a ligand selected to bind to the component, wherein the cross sectional area and bead diameter are selected to maintain a flow velocity of the blood component within the compartment below a first threshold, mixing the at least two blood components together, and returning the mixed blood components to the patient. The first threshold may be selected so as to maintain a force applied by the fluid to the ligand below a second threshold. The ligand may comprise a bond having a strength and maintaining the force below the second threshold may avoid breaking the bond. The force may comprise one or more of a shear force and a moment and the second threshold may comprise one or more of a third threshold related to the shear force and a fourth threshold related to the moment. The ligand may be non-detachably coupled to the beads.

In certain embodiments a ligand comprises one or more linkers or linker elements.

A linker can be covalently attached to a surface of a substrate and to a ligand. In some embodiments, a linker comprises at least one carbon (e.g., a carbon of a substrate surface) and at least one nitrogen (e.g., a nitrogen of a ligand). In some embodiments, at least one carbon of a linker is derived from a surface of a substrate. In some embodiments, at least one carbon of a linker is derived from formyl group of a substrate surface. In some embodiments, at least one nitrogen of a linker is derived from a ligand. In certain embodiments, at nitrogen of a linker is derived from a primary amine of a ligand. In certain embodiments, a linker comprises at least two carbons and one nitrogen. In certain embodiments, a linker comprises one carbon and one nitrogen. In certain embodiments, a linker comprises a single covalent bond that couples a carbon derived from the surface of a substrate to a nitrogen derived from a primary amine of a ligand. In some embodiments, a linker does not comprise oxygen. In some embodiments, a linker does not comprise a double or triple bond. In certain embodiments, a linker does not comprise a carbonyl group. In certain embodiments, a linker does not comprise a sulfur. In certain embodiments, a adsorbent comprises one or more linkers (e.g., a plurality of linkers). In some embodiments, a linker comprises structure (I) shown below:

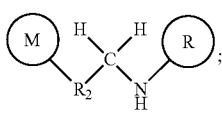

(I)

wherein M is a substrate or substrate surface (e.g., an agarose bead), R is a ligand (e.g., scTNFα), and $R_2$ is absent, an alkyl, a substituted alkyl, a monosaccharide or $CH_2$. In certain embodiments, a linker comprises the structure M-$R_2$—$CH_2$—NH—$R_3$—R or M-$CH_2$—NH—R, where M is a substrate or substrate surface (e.g., an agarose bead), R is a ligand (e.g., scTNFα), and each or $R_2$ and $R_3$ are independently absent, an alkyl or a substituted alkyl. In some embodiments, M (of structure (I) above) or $R_2$ comprises a monosaccharide, polysaccharide or cellulose. In certain embodiments, $R_2$, when present, is not O (oxygen). In some embodiments, $R_3$ comprises an amino acid or amino acid side chain. In certain embodiments, a substrate or substrate surface is attached to a ligand by an amine (e.g., a secondary amine).

In an embodiment, an adsorbent comprises a substrate, a linker and a ligand, wherein the linker is attached to the substrate and the ligand, thereby coupling the substrate to the ligand.

In an embodiment, a column comprises a compartment with a particle disposed within the compartment, the particle comprising a substrate and a ligand bound to the substrate, the ligand comprising at least two monomers each comprising a site that will bind to the target component, a first linker between two of the monomers, and a second linker between one of the monomers and a substrate.

In an embodiment, a method includes one or more of the steps of receiving blood from the patient, separating the blood into at least two blood components, passing a portion of one of the blood components proximate to a ligand comprising at least two monomers each comprising a site that will couple to the component and a first linker coupled by chemical bonds between two of the monomers and a second linker coupled by chemical bonds between one of the monomers and a substrate, mixing the at least two blood components together, and returning the mixed blood components to the patient.

In an embodiment, a method includes one or more of the steps of oxidizing a substrate, forming a Schiff base between a ligand comprising a portion of TNF-alpha and the oxidized substrate, and converting the Schiff base to a secondary amine bond.

Headings and subheadings, if any, are used for convenience only and do not limit the invention.

Reference to an element in the singular is not intended to mean "one and only one" unless specifically so stated, but rather "one or more." Use of the articles "a" and "an" is to be interpreted as equivalent to the phrase "at least one." Unless specifically stated otherwise, the terms "a set" and "some" refer to one or more.

Terms such as "top," "bottom," "upper," "lower," "left," "right," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Pronouns in the masculine (e.g., his) include the feminine and neuter gender (e.g., her and its) and vice versa. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "operation for."

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such as an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

Although embodiments of the present disclosure have been described and illustrated in detail, it is to be clearly understood that the same is by way of illustration and example only and is not to be taken by way of limitation, the scope of the present invention being limited only by the terms of the appended claims.

ADDITIONAL EMBODIMENTS

A1. A column for removal of a component from a fluid, the column comprising:
  a compartment comprising a cross-sectional area;
  a bead having a diameter and disposed within the compartment; and
  a ligand coupled to the bead and selected to bind to the component;
wherein the cross-sectional area and bead diameter are selected to maintain a flow velocity of the fluid within the compartment below a first threshold.

A2. The column of embodiment A1 wherein the bead comprises a plurality of ligands.
A3. The column of embodiment A1 or A2, wherein the ligand comprises a portion of Tumor Necrosis Factor alpha (TNF-alpha).
A4. The column of any one of embodiments A1 to A3, wherein the ligand comprises a trimer of the portions of TNF-alpha.
A5. The column of any one of embodiments A1 to A4, wherein the first threshold is selected so as to maintain an amount of the ligand in the fluid flowing out of the outlet below a predetermined level.
A6. The column of any one of embodiments A1 to A5, wherein the first threshold is selected so as to maintain a force applied by the fluid to the ligand below a second threshold, thereby reducing leaching of the ligand into the fluid.
A7. The column of any one of embodiments A1 to A6, wherein:
the ligand comprises a bond having a strength; and
maintaining the force below the second threshold avoids breaking the bond.
A8. The column of any one of embodiments A1 to A7, wherein:
the bead comprises agarose; and
the bond comprises an amine bond.
A9. The column of any one of embodiments A1 to A8, wherein:
the force comprises one or more of a shear force and a moment; and
the second threshold comprises one or more of a third threshold related to the shear force and a fourth threshold related to the moment.
A10. The column of any one of embodiments A1 to A9, wherein:
the compartment further comprises an inlet, an outlet, and a flow path from the inlet to the outlet;
the flow path has a length; and
the length is selected to provide a contact time between the fluid and the ligand.
A11. The column of any one of embodiments A1 to A10, wherein:
the bead comprises a plurality of beads; and
the ligand comprises a plurality of portions of ligand respectively coupled to each of the plurality of beads.
A12. The column of any one of embodiments A1 to A11, wherein the ligand is non-detachably coupled to the beads.
B1. A method of removing a target component from blood of a patient, comprising the steps of:
receiving blood from the patient;
separating the blood into at least two blood components;
passing a portion of one of the blood components through a compartment having a cross-sectional area and containing a plurality of beads having a diameter and to which are coupled a ligand selected to bind to the component, wherein the cross-sectional area and bead diameter are selected to maintain a flow velocity of the blood component within the compartment below a first threshold;
mixing the at least two blood components together; and
returning the mixed blood components to the patient.
B2. The method of embodiment B1, wherein the first threshold is selected so as to maintain a force applied by the fluid to the ligand below a second threshold.
B3. The method of embodiment B1 or B2, wherein:
the ligand comprises a bond having a strength; and
maintaining the force below the second threshold avoids breaking the bond.
B4. The method of any one of embodiments B1 to B3, wherein:
the force comprises one or more of a shear force and a moment; and
the second threshold comprises one or more of a third threshold related to the shear force and a fourth threshold related to the moment.
B5. The method of any one of embodiments B1 to B4, wherein the ligand is non-detachably coupled to the beads.
C1. A ligand for removal of a component from a fluid, the ligand comprising:
at least two monomers each comprising a site that will couple to the component;
a first linker coupled by chemical bonds between two of the monomers; and
a second linker coupled by chemical bonds between one of the monomers and a substrate.
C2. The ligand of embodiment C1, wherein the ligand comprises three and only three monomers.
C3. The ligand of embodiment C1 or C2, wherein the ligand comprises two and only two first linkers.
C4 The ligand of any one of embodiments C1 to C3, wherein the ligand comprises one and only one second linker.
C5. The ligand of any one of embodiments C1 to C4, wherein the second linker comprises an amine bond.
C6. The ligand of any one of embodiments C1 to C5, wherein the monomer comprises a site that will bind to a cytokine receptor.
C7. The ligand of any one of embodiments C1 to C4, wherein the monomer comprises tumor necrosis factor alpha (TNF-alpha).
D1. A bead for use in removing a component from a fluid, the bead comprising:
a substrate; and
a ligand coupled to the substrate, the ligand comprising:
at least two monomers each comprising a site that will couple to the component;
a first linker coupled between two of the monomers; and
a second linker coupled to one of the monomers and coupled by a chemical bond to the substrate.
D2. The bead of embodiment D1, wherein the substrate is partially oxidized.
D3. The bead of embodiment D1 or D2, wherein the substrate comprises a polysaccharide.
D4. The bead of any one of embodiments D1 to D3, wherein the chemical bond of the second linker comprises an amine bond.
E1 A column for use in removing a component from a fluid, the column comprising:
a compartment;
a bead disposed within the compartment, the bead comprising:
a substrate; and
a ligand coupled to the substrate, the ligand comprising:
at least two monomers each comprising a site that will couple to the component;
a first linker coupled by chemical bonds between two of the monomers; and
a second linker coupled by chemical bonds between one of the monomers and the substrate.

F1. A method of removing a target component from blood of a patient, comprising the steps of:
  receiving blood from the patient;
  separating the blood into at least two blood components;
  passing a portion of one of the blood components proximate to a ligand comprising:
    at least two monomers each comprising a site that will couple to the component;
    a first linker coupled by chemical bonds between two of the monomers; and
    a second linker coupled by chemical bonds between one of the monomers and the substrate;
  mixing the at least two blood components together; and
  returning the mixed blood components to the patient.

G1. A method of preparing an apheresis particle, comprising the steps of:
  oxidizing a substrate;
  forming a Schiff base between a ligand comprising a portion of Tumor Necrosis Factor alpha (TNF-alpha) and the oxidized substrate; and
  converting the Schiff base to a secondary amine bond.

G2. The method of embodiment 31, wherein the step of oxidizing a substrate comprises exposing the substrate to an inorganic salt.

G3. The method of embodiment G2, wherein the inorganic salt comprises sodium metaperiodate.

G4. The method of any one of embodiments G1 to G3, wherein the step of converting the Schiff base to a secondary amine bond comprises exposing the substrate to a reducing agent.

G5. The method of any one of embodiments G1 to G4, wherein the reducing agent comprises sodium cyanoborohydride.

H1. An adsorbent for removing a target component from blood of a subject, the adsorbent comprising:
  a substrate comprising a surface;
  a linker comprising an amine bond; and
  a ligand comprising TNFα;
  wherein the linker is attached to the substrate and to the ligand.

H2. The adsorbent of embodiment H1, wherein the adsorbent comprises structure (I):

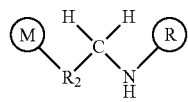

(I)

wherein M is the substrate, R is the ligand, and the linker is —R$_2$—CH$_2$—NH, wherein R$_2$ is absent, an alkyl or substituted alkyl.

H3. The adsorbent of embodiment H2, wherein R$_2$ is CH$_2$.

H4. The adsorbent of any one of embodiments H1 to H3, wherein the substrate comprises a plurality of ligands.

H5. The adsorbent of any one of embodiments H1 to H4, wherein the substrate comprises a particle or a bead.

H6. The adsorbent of any one of embodiments H1 to H5, wherein the substrate comprises a polysaccharide.

H7. The adsorbent of any one of embodiments H1 to H6, wherein the substrate comprises cellulose.

H8. The adsorbent of any one of embodiments H1 to H7, wherein the substrate has a mean, average or absolute diameter in a range of about 60-200 μtn.

H9. The adsorbent of any one of embodiments H1 to H8, wherein the substrate has a mean, average or absolute diameter in a range of about 45-165 μm.

H10. The adsorbent of any one of embodiments H1 to H9, wherein the substrate is porous.

H11. The adsorbent of any one of embodiments H1 to H10, wherein the ligand comprises a trimer comprising at least three monomers of a TNF superfamily ligand.

H12. The adsorbent of embodiment H11, wherein at least two of the three monomers are the same.

H13. The adsorbent of any one of embodiments H1 to H12, wherein the ligand comprises a single chain TNFα.

H14. The adsorbent of any one of embodiments H1 to H13, wherein the N of the linker is derived from a primary amine of the ligand.

H15. The adsorbent of any one of embodiments H1 to H14, wherein the CH$_2$ of the linker is derived from the substrate.

H16. The adsorbent of any one of embodiments H1 to H15, wherein the ratio of the ligand to the substrate is at least 50:1.

H17. The adsorbent of any one of embodiments H1 to H11, wherein the ligand is at least 2-fold, at least 5-fold or at least 10-fold more resistant to dissociation from the substrate relative to a second ligand that is attached to a second substrate by a bond selected from an amide bond, a double bond, a triple bond, NC—NO, C—O, C═O, OC═O, OC—N, N—N, N═N and S—S.

H18. The adsorbent of any one of embodiments H1 to H17, wherein an initial leaching rate of the ligand from the substrate is less than about 10 ng/min, or less than about 5 ng/min at a flow rate of 10 ml/min.

H19. The adsorbent of any one of embodiments H1 to H18, wherein an initial leaching rate of the ligand from the substrate is less than about 50 pg/ml, less than about 25 pg/ml, less than about 20 pg/ml, less than about 10 pg/ml, or less than about 5 pg/ml when measured at a flow rate of 10 ml/min for a period of time of about 2 minutes.

I1. A method of producing the adsorbent of any one of embodiments H1 to H19 comprising: contacting a mixture comprising the ligand and the substrate surface with sodium cyanoborohydride, wherein the ligand comprises at least one primary amine and the substrate surface comprises at least one aldehyde moiety, thereby producing the adsorbent of any one of embodiments H1-H19.

I2. The method of embodiment I1, further comprising, prior to the contacting, oxidizing the substrate surface, thereby forming the at least one aldehyde moiety.

J1. An adsorbent for removing a TNF receptor from blood of a subject, the adsorbent comprising:
  a substrate comprising a substrate surface; and
  a ligand comprising a single chain TNFα;
  wherein the substrate surface is attached to the single chain TNFα by an amine bond.

J2. The adsorbent of embodiment J1, wherein the amine bond is a secondary amine bond.

What is claimed is:

1. A method of preparing an adsorbent, comprising the steps of:
   activating a substrate by exposing the substrate to an activation solution comprising an inorganic salt;
   forming a bond between the activated substrate and a capture ligand by exposing the substrate to a ligand solution comprising the capture ligand, wherein the ligand solution has a pH in the range of 8.5-10; and
   strengthening the bond by exposing the bond to a coupling solution comprising sodium cyanoborohydride, wherein the coupling solution has a pH in the range of 8.5-10 so that the bond forms a secondary amine linkage while avoiding thioether and ether linkages;
   wherein the capture ligand does not comprise an amino acid substitution.

2. The method of claim 1, wherein:
   the substrate comprises agarose; and
   the inorganic salt comprises sodium metaperiodate.

3. The method of claim 1, wherein:
   the capture ligand comprising a portion of Tumor Necrosis Factor alpha (TNF-alpha).

4. The method of claim 3, wherein:
   the portion of TNF-alpha comprises a single-chain TNF-alpha trimer.

5. The method of claim 4, wherein:
   the substrate comprises a plurality of beads; and
   the ligand solution comprises approximately 1 milligram of single-chain TNF-alpha trimer per 1 milliliter of beads when a bed volume of the ligand solution is added to a bed volume of beads.

6. The method of claim 1, further comprising the steps of:
   aspirating the ligand solution and the coupling solution, after the step of strengthening the bond, from the substrate;
   quenching the substrate, after the step of aspirating the ligand solution and the coupling solution, by exposing the aspirated substrate to a quench solution comprising ethanolamine;
   aspirating the quench solution, after the step of quenching, from the substrate thereby producing an aspirated and quenched substrate; and
   adding a phosphate-buffered saline (PBS) solution having a pH in the range of 7.1-7.3, to the aspirated and quenched substrate.

7. The method of claim 1, further comprising the steps of:
   aspirating the ligand solution and the coupling solution, after the step of strengthening the bond, from the substrate; and
   adding a phosphate-buffered saline (PBS) solution having a pH in the range of 7.1-7.3, after the step of aspirating the ligand solution and without quenching the substrate, to the aspirated substrate.

8. An adsorbent, comprising:
   a substrate; and
   a capture ligand that does not comprise an amino acid substitution;
   wherein the adsorbent is prepared by the steps of:
   activating the substrate by exposing the substrate to an activation solution comprising an inorganic salt;
   forming a bond between the activated substrate and the capture ligand by exposing the substrate to a ligand solution comprising the capture ligand, wherein the ligand solution has a pH in the range of 8.5-10; and
   strengthening the bond by exposing the bond to a coupling solution comprising sodium cyanoborohydride, wherein the coupling solution has a pH in the range of 8.5-10 so that the bond forms a secondary amine linkage while avoiding thioether and ether linkages.

9. The adsorbent of claim 8, wherein:
   the capture ligand comprising a portion of Tumor Necrosis Factor alpha (TNF-alpha).

10. The adsorbent of claim 9, wherein:
    the portion of TNF-alpha comprises a single-chain TNF-alpha trimer.

* * * * *

SEQUENCE LISTING

<160> NUMBER OF SEQ ID NOS: 3

<210> SEQ ID NO 1
<211> LENGTH: 155

<212> TYPE: PRT
<213> ORGANISM: Homo sapiens

<400> SEQUENCE: 1

```
Ser Ser Ser Arg Thr Pro Ser Asp Lys Pro Val Ala His Val Ala
1               5                   10                  15

Asn Pro Gln Ala Glu Gly Gln Leu Gln Trp Leu Asn Arg Arg Ala Asn
            20                  25                  30

Ala Leu Leu Ala Asn Gly Val Glu Leu Arg Asp Asn Gln Leu Val Val
        35                  40                  45

Pro Ser Glu Gly Leu Tyr Leu Ile Tyr Ser Gln Val Leu Phe Lys Gly
    50                  55                  60

Gln Gly Cys Pro Ser Thr His Val Leu Leu Thr His Thr Ile Ser Arg
65                  70                  75                  80

Ile Ala Val Ser Tyr Gln Thr Lys Val Asn Leu Leu Ser Ala Ile Lys
                85                  90                  95

Ser Pro Cys Gln Arg Glu Thr Pro Glu Gly Ala Glu Ala Lys Pro Trp
            100                 105                 110

Tyr Glu Pro Ile Tyr Leu Gly Gly Val Phe Gln Leu Glu Lys Gly Asp
        115                 120                 125

Arg Leu Ser Ala Glu Ile Asn Arg Pro Asp Tyr Leu Asp Phe Ala Glu
    130                 135                 140

Ser Gly Gln Val Tyr Phe Gly Ile Ile Ala Leu
145                 150                 155
```

<210> SEQ ID NO 2
<211> LENGTH: 509
<212> TYPE: PRT
<213> ORGANISM: Artificial Sequence
<220> FEATURE:
<223> OTHER INFORMATION: Trimeric peptide

<400> SEQUENCE: 2

```
Met Cys Gly Ser His His His His His Gly Ser Ala Ser Ser Ser
1               5                   10                  15

Ser Arg Thr Pro Ser Asp Lys Pro Val Ala His Val Ala Asn Pro
            20                  25                  30

Gln Ala Glu Gly Gln Leu Gln Trp Leu Asn Arg Arg Ala Asn Ala Leu
            35                  40                  45

Leu Ala Asn Gly Val Glu Leu Arg Asp Asn Gln Leu Val Val Pro Ser
    50                  55                  60

Glu Gly Leu Tyr Leu Ile Tyr Ser Gln Val Leu Phe Lys Gly Gln Gly
65                  70                  75                  80

Cys Pro Ser Thr His Val Leu Leu Thr His Thr Ile Ser Arg Ile Ala
                85                  90                  95

Val Ser Tyr Gln Thr Lys Val Asn Leu Leu Ser Ala Ile Lys Ser Pro
            100                 105                 110

Cys Gln Arg Glu Thr Pro Glu Gly Ala Glu Ala Lys Pro Trp Tyr Glu
        115                 120                 125

Pro Ile Tyr Leu Gly Gly Val Phe Gln Leu Glu Lys Gly Asp Arg Leu
    130                 135                 140

Ser Ala Glu Ile Asn Arg Pro Asp Tyr Leu Asp Phe Ala Glu Ser Gly
145                 150                 155                 160

Gln Val Tyr Phe Gly Ile Ile Ala Leu Gly Gly Ser Gly Gly
                165                 170                 175

Ser Gly Gly Gly Ser Gly Gly Gly Ser Ser Arg Thr Pro Ser Asp
```

```
            180                 185                 190
Lys Pro Val Ala His Val Ala Asn Pro Gln Ala Glu Gly Gln Leu
            195                 200                 205

Gln Trp Leu Asn Arg Arg Ala Asn Ala Leu Leu Ala Asn Gly Val Glu
    210                 215                 220

Leu Arg Asp Asn Gln Leu Val Val Pro Ser Glu Gly Leu Tyr Leu Ile
225                 230                 235                 240

Tyr Ser Gln Val Leu Phe Lys Gly Gln Gly Cys Pro Ser Thr His Val
                245                 250                 255

Leu Leu Thr His Thr Ile Ser Arg Ile Ala Val Ser Tyr Gln Thr Lys
                260                 265                 270

Val Asn Leu Leu Ser Ala Ile Lys Ser Pro Cys Gln Arg Glu Thr Pro
            275                 280                 285

Glu Gly Ala Glu Ala Lys Pro Trp Tyr Glu Pro Ile Tyr Leu Gly Gly
            290                 295                 300

Val Phe Gln Leu Glu Lys Gly Asp Arg Leu Ser Ala Glu Ile Asn Arg
305                 310                 315                 320

Pro Asp Tyr Leu Asp Phe Ala Glu Ser Gly Gln Val Tyr Phe Gly Ile
                325                 330                 335

Ile Ala Leu Gly Gly Gly Ser Gly Gly Gly Ser Gly Gly Gly Ser Gly
                340                 345                 350

Gly Gly Ser Ser Arg Thr Pro Ser Asp Lys Pro Val Ala His Val
            355                 360                 365

Val Ala Asn Pro Gln Ala Glu Gly Gln Leu Gln Trp Leu Asn Arg Arg
370                 375                 380

Ala Asn Ala Leu Leu Ala Asn Gly Val Glu Leu Arg Asp Asn Gln Leu
385                 390                 395                 400

Val Val Pro Ser Glu Gly Leu Tyr Leu Ile Tyr Ser Gln Val Leu Phe
                405                 410                 415

Lys Gly Gln Gly Cys Pro Ser Thr His Val Leu Leu Thr His Thr Ile
                420                 425                 430

Ser Arg Ile Ala Val Ser Tyr Gln Thr Lys Val Asn Leu Leu Ser Ala
                435                 440                 445

Ile Lys Ser Pro Cys Gln Arg Glu Thr Pro Glu Gly Ala Glu Ala Lys
            450                 455                 460

Pro Trp Tyr Glu Pro Ile Tyr Leu Gly Gly Val Phe Gln Leu Glu Lys
465                 470                 475                 480

Gly Asp Arg Leu Ser Ala Glu Ile Asn Arg Pro Asp Tyr Leu Asp Phe
                485                 490                 495

Ala Glu Ser Gly Gln Val Tyr Phe Gly Ile Ile Ala Leu
            500                 505

<210> SEQ ID NO 3
<211> LENGTH: 499
<212> TYPE: PRT
<213> ORGANISM: Artificial Sequence
<220> FEATURE:
<223> OTHER INFORMATION: Trimeric peptide

<400> SEQUENCE: 3

Gly Ser Ala Ser Ser Ser Arg Thr Pro Ser Asp Lys Pro Val Ala
1               5                   10                  15

His Val Val Ala Asn Pro Gln Ala Glu Gly Gln Leu Gln Trp Leu Asn
                20                  25                  30

Arg Arg Ala Asn Ala Leu Leu Ala Asn Gly Val Glu Leu Arg Asp Asn
```

```
            35                  40                  45
Gln Leu Val Val Pro Ser Glu Gly Leu Tyr Leu Ile Tyr Ser Gln Val
             50                  55                  60
Leu Phe Lys Gly Gln Gly Cys Pro Ser Thr His Val Leu Leu Thr His
 65                  70                  75                  80
Thr Ile Ser Arg Ile Ala Val Ser Tyr Gln Thr Lys Val Asn Leu Leu
                 85                  90                  95
Ser Ala Ile Lys Ser Pro Cys Gln Arg Glu Thr Pro Glu Gly Ala Glu
            100                 105                 110
Ala Lys Pro Trp Tyr Glu Pro Ile Tyr Leu Gly Gly Val Phe Gln Leu
            115                 120                 125
Glu Lys Gly Asp Arg Leu Ser Ala Glu Ile Asn Arg Pro Asp Tyr Leu
            130                 135                 140
Asp Phe Ala Glu Ser Gly Gln Val Tyr Phe Gly Ile Ile Ala Leu Gly
145                 150                 155                 160
Gly Gly Ser Gly Gly Gly Ser Gly Gly Gly Ser Gly Gly Gly Ser Ser
                165                 170                 175
Ser Arg Thr Pro Ser Asp Lys Pro Val Ala His Val Val Ala Asn Pro
            180                 185                 190
Gln Ala Glu Gly Gln Leu Gln Trp Leu Asn Arg Arg Ala Asn Ala Leu
            195                 200                 205
Leu Ala Asn Gly Val Glu Leu Arg Asp Asn Gln Leu Val Val Pro Ser
210                 215                 220
Glu Gly Leu Tyr Leu Ile Tyr Ser Gln Val Leu Phe Lys Gly Gln Gly
225                 230                 235                 240
Cys Pro Ser Thr His Val Leu Leu Thr His Thr Ile Ser Arg Ile Ala
                245                 250                 255
Val Ser Tyr Gln Thr Lys Val Asn Leu Leu Ser Ala Ile Lys Ser Pro
            260                 265                 270
Cys Gln Arg Glu Thr Pro Glu Gly Ala Glu Ala Lys Pro Trp Tyr Glu
            275                 280                 285
Pro Ile Tyr Leu Gly Gly Val Phe Gln Leu Glu Lys Gly Asp Arg Leu
            290                 295                 300
Ser Ala Glu Ile Asn Arg Pro Asp Tyr Leu Asp Phe Ala Glu Ser Gly
305                 310                 315                 320
Gln Val Tyr Phe Gly Ile Ile Ala Leu Gly Gly Ser Gly Gly Gly
                325                 330                 335
Ser Gly Gly Gly Ser Gly Gly Gly Ser Ser Arg Thr Pro Ser Asp
            340                 345                 350
Lys Pro Val Ala His Val Val Ala Asn Pro Gln Ala Glu Gly Gln Leu
            355                 360                 365
Gln Trp Leu Asn Arg Arg Ala Asn Ala Leu Leu Ala Asn Gly Val Glu
            370                 375                 380
Leu Arg Asp Asn Gln Leu Val Val Pro Ser Glu Gly Leu Tyr Leu Ile
385                 390                 395                 400
Tyr Ser Gln Val Leu Phe Lys Gly Gln Gly Cys Pro Ser Thr His Val
                405                 410                 415
Leu Leu Thr His Thr Ile Ser Arg Ile Ala Val Ser Tyr Gln Thr Lys
            420                 425                 430
Val Asn Leu Leu Ser Ala Ile Lys Ser Pro Cys Gln Arg Glu Thr Pro
            435                 440                 445
Glu Gly Ala Glu Ala Lys Pro Trp Tyr Glu Pro Ile Tyr Leu Gly Gly
            450                 455                 460
```

```
                                    -continued

Val Phe Gln Leu Glu Lys Gly Asp Arg Leu Ser Ala Glu Ile Asn Arg
465                 470                 475                 480

Pro Asp Tyr Leu Asp Phe Ala Glu Ser Gly Gln Val Tyr Phe Gly Ile
                485                 490                 495

Ile Ala Leu
```